(12) United States Patent
Larreta-Garde et al.

(10) Patent No.: US 8,206,945 B2
(45) Date of Patent: Jun. 26, 2012

(54) BIOMATERIAL CAPABLE OF SUCCESSIVELY PERFORMING A SOLUTION/GEL TRANSITION AND THEN A GEL/SOLUTION TRANSITION

(75) Inventors: Véronique Larreta-Garde, L'Isle Adam (FR); Sébastien Giraudier, Cergy (FR)

(73) Assignee: Université de Cergy-Pontoise (FR)

( * ) Notice: Subject to any disclaimer, the term of this patent is extended or adjusted under 35 U.S.C. 154(b) by 892 days.

(21) Appl. No.: 11/720,089

(22) PCT Filed: Nov. 25, 2005

(86) PCT No.: PCT/FR2005/002939
§ 371 (c)(1),
(2), (4) Date: Aug. 6, 2008

(87) PCT Pub. No.: WO2006/056700
PCT Pub. Date: Jun. 1, 2006

(65) Prior Publication Data
US 2009/0029411 A1    Jan. 29, 2009

(30) Foreign Application Priority Data
Nov. 26, 2004    (FR) ...................................... 04 52774

(51) Int. Cl.
*C12P 21/00*    (2006.01)
(52) U.S. Cl. ......................................... 435/68.1; 435/7.1
(58) Field of Classification Search .................. None
See application file for complete search history.

(56) References Cited

U.S. PATENT DOCUMENTS
5,279,839 A    1/1994  Gottmann et al.
5,702,717 A *  12/1997 Cha et al. ...................... 424/425

FOREIGN PATENT DOCUMENTS
EP    0 492 406    7/1992
WO    WO 97/40701   4/1997

OTHER PUBLICATIONS

Sigmund, (J. Am. Ceram. Soc., vol. 83, No. 7, pp. 1557-1574, 2000).*
Berry, et al., *Biochim. Biophys. Acta.*, 1524:110-117, 2000.
Berry, et al., *Biochimica et Biophysica Acta*, 1524(2-3):110-117, 200.
Bronson, et al., *Equations Différentielles*, Mc Graw-Hill ed, 233-234, 1994.
Crescenzi, et al., *Biomacromolecules*, 3(6):1384-1391, 2002.
Fadda, et al., *Biophys. J.*, 85(5):2808-2817, 2003.
Fuchsbauer, et al., *Biomaterials*, 17:1481-1488, 1999.
Giraudier, et al., *Biomacromolecules*, 5(5);1662-1666, 2004.
Joly-Duhamel, et al., *Langmuir*, 18:7158-7166, 2002.
Joly-Duhammel, et al., *Langmuir*, 18:7208-7217, 2002.
Larreta-Garde, et al., *Communication Arachon Mars, Activites Enzymatiques Antagonistes Dans le Remodelage de la Matrice Extracellulaire*, 2004.
Larreta-Garde, et al., *Communication Rome, Session No. Transglutaminases, n 6, Contribution of Helices and Transglutaminase-catalyzed covalent bonds to gelatin networks*, 2003.
Larreta-Garde, et al., *J. Theor. Biol.*, 217:105-124, 2002.
Ligne, et al., *Biochim. Biophys. Acta.*, 1337:143-148, 1997.
Matsubara, et al., *Biochem. Biophys. Res. Commun.*, 21:242-247, 1965.
Persikov, et al., *Biochemistry*, 39:14960-14967, 2000.
Vera-Avila, et al., *Journal of Sol-Gel Science and Technology*, 30(3):197-204.

* cited by examiner

*Primary Examiner* — Hope Robinson
(74) *Attorney, Agent, or Firm* — Choate Hall & Stewart LLP; Brenda Herschbach Jarrell

(57) ABSTRACT

The invention relates to a biomaterial which can successively carry out a solution/gel transition then a gel/solution transition with given kinetics, said biomaterial comprising at least one monomer which may form polymers, at least one enzyme which may decompose said polymers and, optionally, an enzyme which may form covalent bonds between said monomers. The invention further relates to a method for the production of said biomaterial.

10 Claims, 14 Drawing Sheets

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: hydrolyzed by collagenase
<220> FEATURE:
<221> NAME/KEY: misc_feature
<222> LOCATION: (2)..(2)
<223> OTHER INFORMATION: Xaa can be any naturally occurring amino
      acid

<400> SEQUENCE: 1

Pro Xaa Gly Pro
1

<210> SEQ ID NO 2

```
<211> LENGTH: 4
<212> TYPE: PRT
<213> ORGANISM: Artificial Sequence
<220> FEATURE:
<223> OTHER INFORMATION: catalysed hydrolysis reactant

<400> SEQUENCE: 2

Leu Gly Pro Ala
 1
```

BIOMATERIAL CAPABLE OF SUCCESSIVELY PERFORMING A SOLUTION/GEL TRANSITION AND THEN A GEL/SOLUTION TRANSITION

PRIORITY

The present Application is being filed under 35 U.S.C. §371 and claims priority to International Application PCT/FR2005/002939 filed on Nov. 25, 2005; which claims priority to Application No. FR 04/52774 filed Nov. 26, 2004. The entire contents of the above-referenced Applications are hereby incorporated by reference.

FIELD OF THE INVENTION

The present invention relates, for the field of gelling, to a biomaterial that is capable of successively performing a controlled solution/gel transition and then a gel/solution transition and a method of preparing such biomaterial.

BACKGROUND OF THE INVENTION

Gels are used due to their specific properties in numerous fields, in particular food, cosmetic and pharmaceutical. A gel consists of at least two components of which one, clearly the majority, corresponds to the liquid solvent and the other is a component that can be classified as a solid dispersed within the solvent. Based on a solution or a dispersion in liquid state, the formation of the gel results from partial aggregation of solid particles. This transformation is called the solution/gel transition.

Compositions for obtaining "physical" gels are well known in the prior art. A physical gel is a macromolecular assembly made up of monomers bonded to each other by low-energy bonds (Van der Waals, hydrogen bonds, polar bonds, etc.). This stability of this assembly is associated with a certain range of physico-chemical conditions (pH, monomer concentration, temperature, solvent quality, ionic force, etc.). Outside this range, the gel becomes a solution again. The solution/gel transition is therefore reversible for physical gels. Thus, the structure of physical gels is highly sensitive to the physico-chemical environment and a very slight change in the quality of the solvent can entirely demolish this structure and thereby produce a gel-solution transition. Conversely, the polymeric association resulting in the gel can be carried out by a slight change in the quality of the solvent.

Gels classified as "chemical" are also known in the prior art. A chemical gel is also a macromolecular assembly, and the monomers it contains are associated by high-energy bonds (covalent). This assembly is therefore very stable. But for all that, while these chemical gels have increased stability, the only way to perform a gel/solution transition consists of destroying the covalent bonds of the polymer. This is why a gel/solution transition of this type is called irreversible.

The chemical gel family corresponds to the enzymatically catalysed gels. This gelling mode is mainly observed in major biological processes. Blood coagulation, cicatrisation, skin formation and the assembly of extracellular matrices are biological processes in which the transition from soluble proteins to gel state is essential, and they share a family of enzymes: transglutaminases (TGases), which are essential in gelling processes. This family of proteins is ubiquitous and can be found equally in prokaryotes and in eukaryotes. Eight different TGases can be found in humans. These enzymes have the property of including amine groups on glutaminyl side chains of proteins. This activity makes it possible to form covalent bonds between the proteins. TGases thus catalyse the polymerisation of the proteins responsible for the formation of biological gelled networks. TGases make it possible to obtain gels from numerous proteins in the food industry, in particular for manufacturing surimi or for hardening numerous meat derivatives (ham, reconstituted food, etc.). Examples of these polymerisable proteins include gelatine, fibrin, gliadin, myosin, globulin (7S and 11S), actin, myoglobin, whey proteins, in particular caseins and lactoglobulin, soy and wheat proteins and, in particular, glutenin, egg white and yolk and, in particular, egg albumin.

One of the most commonly used protein gels is gelatine gel. Gelatine is obtained from collagen, which is a protein with a ubiquitous structure. Collagen can be found in soluble state in the form of monomers or trimers associated in triple helix formation. These triple helices can associate as fibrils which can associate as fibres. The collagen triple helix is unstable at body temperature. Gelatine is obtained by collagen denaturation. Tissue containing collagen is therefore subjected to acid or alkaline treatment, which denatures the collagen triple helix. The possibility of forming fibres is therefore completely lost. Acid treatment results in the formation of type-A gelatine and alkaline treatment produces a type-B gelatine. The gelatine solution therefore consists of isolated collagen chains (collagen monomers). Since gelatine has many uses, it is sometimes necessary to create gelatine gels in conditions where physical gels cannot exist (high temperatures, extreme pH or specific ionic force). To form the network required for the gel, the gelatine chains are then interlaced by covalent bonds and, in particular, by the action of the TGases. The gels thus obtained are chemical gels.

Many fields currently require the use of chemical gels due to their improved stability. However, their "irreversibility" restricts their potential uses in the cosmetics, food or even pharmaceutical industries. Greater control over the mechanical properties of the various gels therefore constitutes an essential issue for increasing their potential.

DETAILED DESCRIPTION OF CERTAIN PREFERRED EMBODIMENTS OF THE INVENTION

Figure 1:
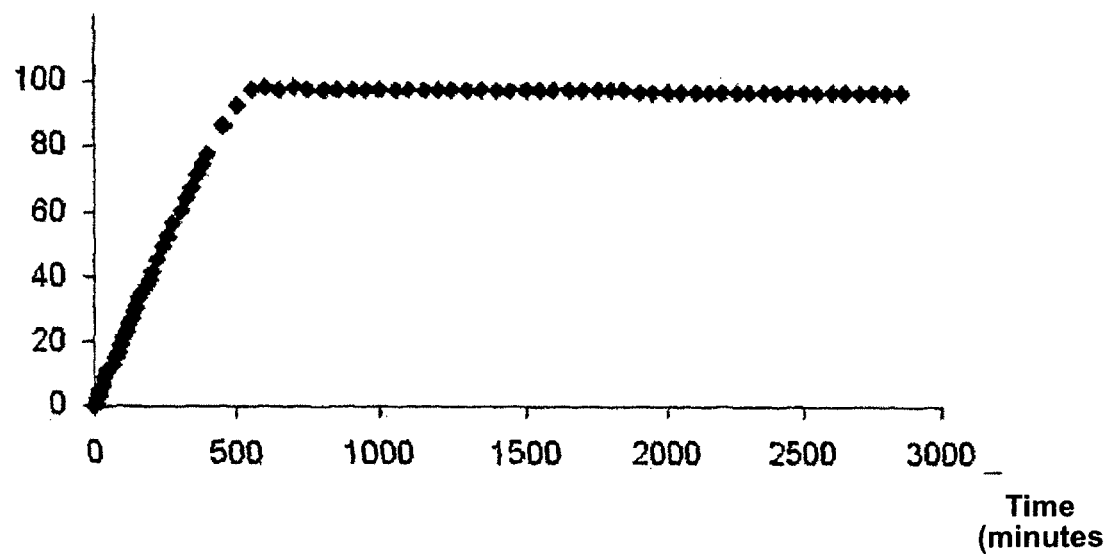
FIG. 1 relates to Example 1, section 2-Transglutaminase, and shows an example of modelling the evolution of the bonded fraction in time, with a $V'_p/V_p$ ratio of 0.1.

An analysis of living organisms shows the existence of extremely dynamic systems. In living tissue, cells interact with a structure called the extracellular matrix (ECM), which is rich in proteins. This structure is mainly located under epithelial cells and around connective tissue. Cells can synthesise various components of the extracellular matrix, such as collagen, which affects elasticity, or fibronectin, which affects adherence mechanisms. At the same time, the cell also produces proteases which affect the degradation of the extracellular matrix. The cell therefore has a simultaneous effect on the construction and degradation of the extracellular matrix. The structure of the extracellular matrix is not therefore an irreversible, static structure, but rather corresponds to a dynamic balance resulting from the balance between the activities of construction and degradation of proteins synthesised by the cell.

In the same way, clots formed in response to the coagulation mechanism also constitute dynamic systems. Thus, the synthesis of a cascade of enzymatic factors causes the formation of an insoluble clot that resulting from the formation of a network of soluble proteins. This clot is later eliminated during the cicatrisation reaction.

In these dynamic balances, the protein networks associate to become insoluble and form gels, which can be compared with solution/gel transitions. At the same time, protein networks are also destroyed by the action of proteases, this type of transition in this case being comparable with gel/solution transitions. It is therefore sometimes possible to see successive transitions, such as in coagulation, where the clot is initially formed and then degraded to give way to other reactions according to poorly understood mechanisms.

The solution/gel transition in these biological processes is most often associated with the transglutaminase family described above. The opposite transition, namely gel/solution is, on the other hand, associated with the antagonist activity of proteolytic enzymes.

One of the most studied families is that of matrix metalloproteinases (MMP). They form a family of zinc-dependent endopeptidases, which degrade most of the proteins in the extracellular matrix. However, a large number of different protease families exists. Examples of protease families include serin proteases, such as trypsin, matriptase, cysteines and aspartate proteases, such as cathepsins B and L and cathepsins D and G, and the ADAM family.

A large number of enzymes that orchestrate this type of reaction, such as transglutaminases or even metalloproteases, have been characterised by biochemists and enzymologists. The description of these enzymes and, in particular, of the different constants associated with them, is therefore well controlled. Moreover, although their behaviour is known in a solution and in isolation, this is not the case in gel environments and in the presence of an antagonist activity.

The modelling work conducted by the inventors and other teams has made it possible to understand the parameters involved in this dynamic balance that exists in vivo. The most recent modelling and experimentation work performed by the inventors has allowed them to develop a new model of this dynamic balance which integrates with greater accuracy the parameters involved therein.

Surprisingly, the modelling performed by the inventors has shown that it was possible to obtain such dynamic balance "in vitro". The inventors were therefore able to obtain protein gels that are capable of successively performing solution/gel and gel/solution transitions under given conditions and, in particular, following given kinetics.

Therefore, in a first aspect, the invention relates to a biomaterial that comprises at least one monomer capable of forming polymers, preferably with low-energy bonds, or a mix of said monomer and their polymers, and a first type of enzyme capable of degrading said polymers, said biomaterial being presented either in the form of a gel or in the form of a solution, and being capable of successively performing a first solution/gel transition and then, under the action of a first type of enzyme, a second gel/solution transition.

Such a biomaterial therefore makes it possible to develop products with previously unknown properties in the cosmetic, food or pharmaceutical industries.

In the field of cosmetics, the biomaterial according to the invention can therefore be used to manufacture new cosmetics, such as beauty masks that can adopt the texture of a gel during the required application time before returning to solution state, allowing quick and easy removal by the user.

In the field of food and agriculture, the biomaterial according to the invention can therefore be used to manufacture new products with unknown textures, such as filled biscuits or sweets, in which the filling can be in gel form during the coating process before returning to the more or less viscous solution state once the coating process is ended.

In the field of pharmaceuticals or cosmetics, the biomaterial according to the invention can also be used to obtain gels containing an active ingredient, capable of salting out said active ingredient by returning to solution state with given kinetics. The use of enzymes that are capable of degrading the proteins (i) polymerised in specific temperature, pH and ionic concentration conditions (calcium, magnesium or others) or in the presence of certain cofactors makes is possible to adapt this salting out to a specific environment (intestine, stomach, etc.).

Therefore, the invention also relates to cosmetic, pharmaceutical or food compositions. These compositions can also comprise other agents, such as active agents for cosmetic or pharmacological compositions, or formulation agents for food compositions.

In certain embodiments, the monomer included in the biomaterial is a protein or a saccharide, which can be natural or synthetic.

The first type of enzyme is present in the biomaterial in non-inactivated form. The first type of enzyme capable of degrading the polymers can be in an active form in the biomaterial or in a form that can be activated under specific conditions, such as a given pH, in the presence of an ionic species or a specific co-factor, so as to obtain the gel/solution transition under specific conditions, such as in a specific organ (stomach, intestine, oral cavity, etc.) or in a specific environment.

According to a first specific embodiment of the biomaterial of the invention, the biomaterial also comprises a solvent that is suitable for allowing polymerisation of the monomer and degradation of the polymer formed by the first type of enzyme. The solvent used is preferably an aqueous solvent, such as water or other buffer solutions with the desired pH, (phosphate or tris buffer).

According to a second specific embodiment of the biomaterial of the invention, said biomaterial in gel form is lyophilised using techniques known to those skilled in the trade. The biomaterial does not then contain any solvent. The second gel/solution transition then only takes place once said biomaterial has been placed in contact with a suitable solvent. This embodiment therefore makes it possible to associate the useful life of the gel, after manufacturing, with its presence in a given environment or in a specific organ (stomach, intestine, oral cavity, etc.).

According to a preferred embodiment of the invention, the biomaterial also comprises at least one second type of enzyme capable of forming covalent bonds between said monomers, said biomaterial is then capable of successively performing a first solution/gel transition under the action of the second type of enzyme followed by a second gel/solution transition under the action of the first type of enzyme.

In certain embodiments, the two types of enzymes are present simultaneously in the biomaterial in non-inactivated form.

In certain other embodiments, the enzymes are evenly distributed in the biomaterial.

According to a third specific embodiment of the biomaterial of the invention, the biomaterial comprises a protein monomer. Almost all proteins are capable of forming physical gels thanks to their polyelectrolyte properties.

Examples of proteins that are capable of polymerising to form physical gels and which can be used in the method according to the invention, include collagen and its derivatives, such as gelatine, fibrin, gliadin, myosin, globulin (7S and 11S), actin, myoglobin, whey proteins, in particular caseins and lactoglobulin, soy and wheat proteins and, in particular, glutenin, egg white and yolk and, in particular, egg albumin. The polymerisable proteins used are preferably chosen from among fibrin and collagen and its derivatives, such as type A and B gelatine. In the presence of enzymes capable of forming covalent bonds between protein monomers, it is possible to use proteins that do not naturally polymerise.

The concentration of polymerisable proteins, in the form of monomers or a mix of said monomers and their polymers, in the biomaterial depends on the nature of the proteins used. The concentration of polymerisable proteins is preferably comprised between 0.1 and 30% by weight in relation to the total weight of the biomaterial, preferably between 0.2 and 20%, even more preferably between 0.5 and 15%, and in a particularly preferred manner, between 1 and 10%.

Numerous enzymes capable of degrading protein polymers (proteases) are known to those skilled in the trade. Examples of such enzymes include metalloproteinases, such as metalloproteinases of the MMP family or similar metalloproteinases such as thermolysin, serin proteases, such as trypsin and matriptase, cysteines and aspartate proteases, such as cathepsins B and L and cathepsins D and G, and the ADAM family. The enzyme capable of degrading protein polymers is preferably a metalloproteinase, preferably a thermolysin, in particular bacterial, and in a particularly preferred manner, a thermolysin isolated from *Bacillus thermoproteolyticus rokko*.

The concentration of enzymes capable of degrading the protein polymers depends on the protein monomer used and on the concentration of the latter. This enzyme concentration can be easily calculated by a given type of protein monomer and at a given concentration, according to the method described in the following examples. Thus, in the case of the *Bacillus thermoproteolyticus rokko* thermolysin and for a gel with 5% of type-A gelatine, the thermolysin concentration is greater than or equal to $10^{-4}$ U/ml, preferably greater than or equal to $10^{-3}$ U/ml.

Numerous proteins also capable of forming covalent bonds between proteins are known to those skilled in the trade. Examples of such proteins include the lysyl oxidase family and the transglutaminase family, such as sub-unit A of factor XIII, mammalian TGases 1 to 7 or even bacterial TGases. The enzyme capable of creating covalent bonds between proteins is a transglutaminase, preferably a bacterial transglutaminase and, in a particularly preferred manner, a transglutaminase isolated from *Streptoverticillium* sp.

The concentrations of enzyme capable of forming covalent bonds between proteins and those capable of degrading protein polymers depend, on the one hand, on the ratio of the concentration of enzymes capable of forming covalent bonds between proteins to the concentration of enzymes capable of degrading protein polymers and, on the other hand, on the polymerisable protein used and the concentration of the latter. These enzyme concentrations can be calculated easily according to the method described in the examples.

The ratio of enzyme concentrations and the enzyme concentrations used also depend on the desired gel time (solution/gel transition) and useful gel life.

In certain embodiments, the ratio of the concentration of enzymes capable of forming covalent bonds between proteins to the concentration of enzymes capable of degrading protein polymers is greater than or equal to 1, preferably greater than or equal to 10, and in a particularly preferred manner, greater than or equal to 20.

In certain other embodiments, the concentration of enzymes capable of forming covalent bonds between the proteins is greater than 0.001 U/ml, preferably greater than 0.01 U/ml and in a particularly preferred manner, greater than 0.1 U/ml.

In certain embodiments, and in the case of a solution with 5% type-A gelatine and in the presence of the *Streptoverticillium* sp transglutaminase and the *Bacillus thermoproteolyticus rokko* thermolysin, the ratio of the transglutaminase concentration in U/ml to the thermolysin concentration in U/ml is greater than 75, preferably greater than or equal to 80. In addition, the transglutaminase concentration is greater than or equal to 0.01 U/ml, preferably greater than or equal to 0.1 U/ml and, in a particularly preferred manner, greater than or equal to 0.4 U/ml.

According to a fourth specific embodiment of the present invention, the biomaterial according to the invention comprises a saccharide monomer. Examples of saccharides that can be used by the biomaterial according to the invention include carrageenans, alginates, pectins, chitosan, cellulose, chitin, glycogen or even starch.

The concentration of polymerisable saccharides, in the form of monomers or a mix of said monomers and their polymers, in the biomaterial depends on the nature of the saccharide used. The concentration of polymerisable saccharides is preferably comprised between 0.1 and 30% by weight in relation to the total weight of the biomaterial, preferably between 0.2 and 20%, even more preferably between 0.5 and 15%, and in a particularly preferred manner, between 1 and 10%.

Numerous enzymes capable of degrading polysaccharides are known to those skilled in the trade. Examples of such enzymes include carrageenans, pectin lyase, polygalacturonase and pectin esterase for pectins, alginate lyases for alginates, cellulases for cellulose or even phosphorylase for glycogen.

The concentration of enzymes capable of degrading the polysaccharides depends on the monomer used and on the concentration of the latter. This enzyme concentration can be easily calculated by a given type of monomer and at a given concentration, according to the method described in the examples.

Numerous enzymes also capable of forming covalent bonds between saccharides are known to those skilled in the trade. Examples of such enzymes include the family of alginate epimerases for alginates, synthases for cellulose, or even glycogen synthase for glycogen.

The concentrations of enzyme capable of forming covalent bonds between saccharides and those capable of degrading polysaccharides depend, on the one hand, on the ratio of the concentration of enzymes capable of forming covalent bonds between saccharides to the concentration of enzymes capable of degrading polysaccharides and, on the other hand, on the polymerisable saccharide used and the concentration of the latter. These enzyme concentrations can be calculated easily according to the method described in the examples.

As above, the ratio of enzyme concentrations and the enzyme concentrations used also depend on the desired gel time (solution/gel transition) and useful life of the gel.

In certain embodiments, the ratio (concentration of enzymes capable of forming covalent bonds between saccharides)/(concentration of enzymes capable of degrading polysaccharides) is greater than or equal to 1, preferably greater than or equal to 10, and in a particularly preferred manner, greater than or equal to 20.

In certain other embodiments, the concentration of enzymes capable of forming covalent bonds between the saccharides is greater than 0.001 U/ml, preferably greater than 0.01 U/ml and in a particularly preferred manner, greater than 0.1 U/ml.

According to a fifth specific embodiment of the invention, the biomaterial according to the invention comprises a saccharide monomer and a protein monomer. Such a compound makes it possible to obtain a gel having specific rheological properties and, potentially, a gel having a desired texture.

The biomaterial can also comprise one or more extra components currently used in the cosmetic, pharmaceutical or food industries.

In a second aspect, the invention relates to a method of preparing a biomaterial according to the invention, which is presented in gel form or in solution form and which is capable of successively performing a solution/gel transition followed by a second gel/solution transition, characterised in that it comprises the mix in a suitable solvent:
  (i) of at least one monomer capable of forming polymers, preferably by means of low-energy bonds;
  (ii) of a first type of enzyme capable of degrading said polymers.

The concentration of monomers capable of forming polymers, preferably by low-energy bonds, and the concentration of enzymes capable of degrading said polymers to obtain a biomaterial which has the desired gel time and useful gel life are determined according to the method described in the examples.

As an example, a biomaterial comprising 5% of type-A gelatine, as a monomer capable of forming polymers with low-energy bonds, and thermolysin isolated from *Bacillus thermoproteolyticus rokko* and having a gel time of 68 minutes and a useful gel life of 254 minutes can be obtained at 27° C. using 0.0085 U/ml of thermolysin.

According to a preferred embodiment, the method according to the invention also includes the mix:
  (iii) of a second type of enzyme capable of forming covalent bonds between monomers.

The concentration of monomers capable of forming polymers, optionally by low-energy bonds, the concentration of enzymes capable of degrading said polymers and the concentration of enzymes capable of forming covalent bonds between said monomers, to obtain a biomaterial which has the desired gel time and useful gel life are determined according to the method described in the examples.

The method is carried out at a temperature at which both enzyme types are active. In certain embodiments, the method is performed at a temperature comprised between 0 and 100° C., preferably between 5 and 75° C., for example between 10 and 50° C. or between 15 and 45° C. and, in a particularly preferred manner, between 20 and 40° C.

In certain embodiments, the quantity of monomers capable of forming polymers is comprised between 0.1 and 30% by weight in relation to the total weight of the biomaterial, preferably between 0.2 and 20%, even more preferably between 0.5 and 15%, and in a particularly preferred manner, between 1 and 10%.

In certain embodiments, the ratio of the concentration of enzymes capable of forming covalent bonds between the monomers to the concentration of enzymes capable of degrading the polymers is greater than or equal to 1, preferably greater than or equal to 10, and in a particularly preferred manner, greater than or equal to 20.

The concentration of enzymes capable of forming covalent bonds between the monomers is preferably greater than 0.001 U/ml, preferably greater than 0.01 U/ml and in a particularly preferred manner, greater than 0.1 U/ml.

In certain embodiments, the concentration of monomers capable of forming polymers, the concentration of enzymes capable of degrading said polymers and, possibly, the concentration of enzymes capable of forming covalent bonds between said monomers are chosen so that the result of the following equations (I), (II), (III) and (IV) yields a desired gel time and useful gel life:

$$\frac{dg}{dt} = -\frac{V_P}{K_P + g} \times g + \frac{V_T}{K_T + s} \times s + V_S \quad \text{(I)}$$

$$\frac{ds}{dt} = \frac{V_P}{K_P + g} \times g - \frac{V_T}{K_T + s} \times s - \frac{V'_P}{K_P + s} \times s - V_H \quad \text{(II)}$$

$$\frac{df}{dt} = \frac{V'_P}{K_P + s} \times s \quad \text{(III)}$$

$$g_t + s_t + f_t = s_0 \quad \text{(IV)}$$

equations which respectively describe the evolution of the number of monomers bonded (dg) (I), the evolution of the number of monomers in solution (ds) (II) and the evolution of the number of monomers degraded (df) according to time (dt) (III), and the mass conservation equation (IV), wherein:

g corresponds to the quantity of monomers in bonded form, t corresponds to time, $V_p$ corresponds to the speed of the enzyme capable of degrading the polymers expressed as a quantity of bonded monomers changed to their free form by said enzyme and by unit of time, $K_p$ represents the Michaelis constant of the enzyme capable of degrading the polymers, s represents the quantity of monomers in free form, $V_T$ corresponds to the speed of the enzyme capable of forming covalent bonds between the monomers expressed as a quantity of bonded monomers in free form bonded by said enzyme and by unit of time, $K_T$ represents the Michaelis constant of the enzyme capable of forming covalent bonds between the monomers, $V_H$ represents the speed of bonding, by low-energy bonds and by unit of time, monomers in free form, in the case of monomers capable of polymerising by such bonds, $V'_p$ corresponds to the speed of the enzyme capable of degrading the monomers in free form expressed as a quantity of degraded monomers, which can no longer polymerise, generated by said enzyme and by unit of time, $g_t$ corresponds to the quantity of monomers in bonded form in time t, $s_t$ corresponds to the quantity of monomers in free form in time t, $f_t$ corresponds to the quantity of degraded monomers that are no longer capable of forming polymers in the time t, $S_0$ corresponds to the initial quantity of monomers.

Using different types of enzymes, the inventors have been able to prove that it is possible to obtain biomaterials with given solution/gel and gel/solution transition kinetics.

The constants for these various enzymes are well known to those skilled in the trade. An example of this is the database at www.brenda.uni-koeln.de/, which describes such enzymatic constants. In every case, those skilled in the trade can easily determine these various constants for given enzymes according to well-known methods, such as those described in www.brenda.uni-koeln.de/ and in PRICE and STEVEN, Fundamentals of Enzymology: The Cell and Molecular Biology of Catalytic Proteins, Oxford University Press.

In these equations, VP and VT are therefore calculated according to the following formulae:

$V_P = k_{CAT\_P}[P]$ and $V_T = k_{CAT\_T}[T]$, where [P] and [T] respectively represent the concentrations of enzyme capable of degrading the polymers and enzyme capable of forming covalent bonds between the monomers, and $k_{CAT\_P}$ and $k_{CAT\_T}$ represent the catalytic constants for these enzymes.

In every case, those skilled in the trade can easily determine, without excessive experimentation, following the methods described in the examples, the various monomer and enzyme concentrations required to obtain a biomaterial having the desired solution/gel and gel/solution transition kinetics.

As an example, a biomaterial comprising 5% of type-A gelatine, as a monomer capable of forming polymers with low-energy bonds, thermolysin isolated from *Bacillus thermoproteolyticus rokko*, transglutaminase isolated from *Streptoverticillium* sp and having a gel time of 19 minutes and a useful gel life of 743 minutes can be obtained at 40° C. using 1 U/ml of transglutaminase and 0.0125 U/ml of thermolysin.

As a further example, a biomaterial comprising 5% of type-A gelatine, as a monomer capable of forming polymers with low-energy bonds, thermolysin isolated from *Bacillus thermoproteolyticus rokko*, transglutaminase isolated from *Streptoverticillium* sp and having a gel time of 2 minutes and a useful gel life of more than 5000 minutes can be obtained at 27° C. using 1 U/ml of transglutaminase and 0.0125 U/ml of thermolysin.

In certain embodiments, the method according to the invention comprises a step of lyophilising the biomaterial in gel form.

Further characteristics of the invention will emerge from the following examples, which do not limit the invention in any way whatsoever.

EXEMPLIFICATION

Example 1

Chemical Gel 1-1: Development of a Theoretical Model:

A study of the dynamic balance corresponding to the extracellular matrix has made it possible to draw up a simplified mathematical model of such a dynamic system, wherein two antagonising enzymatic reactions are implemented. One is catalysed by an enzyme capable of forming covalent bonds between the soluble monomers (s) to obtain a network of bonded monomers (g). The other one is catalysed by an enzyme (P) which hydrolyses the network of bonded monomers (g) in soluble monomers (s). Finally, in certain cases, a third reaction also catalysed by the enzyme (P) consists of hydrolysing soluble monomers in degraded monomers (f) that are too small to be included in the network or which can no longer be used as a substrate for the enzyme bonding the soluble monomers (s) by covalent bonds (T). This last reaction which results in monomers leaking from the cycle is also added to the model. The model can be easily represented according to the following reaction scheme:

Scheme I:
Enzyme degrading the chains of bonded monomers (P)

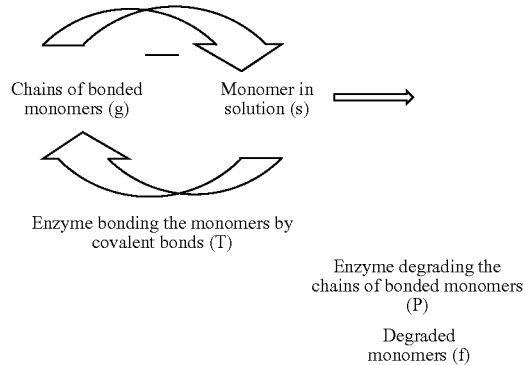

Chains of bonded monomers (g)     Monomer in solution (s)

Enzyme bonding the monomers by covalent bonds (T)

Enzyme degrading the chains of bonded monomers (P)

Degraded monomers (f)

This reaction mechanism can be easily described by the following three differential equations, where the enzymatic reactions are compared with simple Michaelian reactions, and by a fourth mass conservation equation.

The differential equation that describes the evolution of the number of chains of bonded monomers (g) according to time is as follows:

$$\frac{dg}{dt} = -\frac{V_P}{K_P + g} \times g + \frac{V_T}{K_T + s} \times s$$

The differential equation that describes the evolution of the number of monomers in solution (s) according to time is as follows:

$$\frac{ds}{dt} = \frac{V_P}{K_P + g} \times g - \frac{V_T}{K_T + s} \times s - \frac{V'_P}{K_P + s} \times s$$

The differential equation that describes the evolution of the number of degraded monomers (f) according to time is as follows:

$$\frac{df}{dt} = \frac{V'_P}{K_P + s} \times s$$

Finally, the mass conservation equation is as follows:

$$g_t + s_t + f_t = S_0$$

In these differential equations, $V_P$ and $V_T$ represent the maximum speeds for the enzymes P and T respectively and $K_P$ and $K_T$ represent the Michaelis constants for the enzymes P et T respectively.

In these equations, $V_P$ and $V_T$ are therefore calculated according to the following equations:

$$V_P = k_{CAT\_P}[P] \text{ and } V_T = k_{CAT\_T}[T]$$

In the transposition of this equation to an in vitro system, the various values of [P], [T], $V_p$, $V_T$, $K_P$ and $K_T$ are constants.

The substrate concentrations are calculated for each initial enzyme, and are then determined during the reaction by means of the various differential equations.

1-2: Modelling the Formation of a Gelatine Gel in the Presence of a Transglutaminase and Thermolysin This theoretical model was applied to the formation of a physical protein gel, and more specifically of gelatine at 40° C. in the presence of a bacterial transglutaminase, which bonds the gelatine monomers by covalent bonds, and a protease: thermolysin.

The gelatine concentration used is 5%, or 50 g.l$^{-1}$. Based on the peptide sequence of the gelatine, it is possible easily to determine the concentration of side chains, namely 0.45 mol.l$^{-1}$.

Enzymes Used:

The various constants for protease and transglutaminase are known in the literature or can be easily determined according to techniques which are well known to those skilled in the trade (SEGEL, Wiley Classics Library, Enzyme Kinetics, 1993).

1-Protease:

1.1—Source: The protease used is thermolysin, a bacterial metalloprotease marketed by SIGMA (REF: P-1512). This enzyme is a type X protease taken from *Bacillus thermoproteolyticus rokko* which is a thermophilic bacterial strain. This enzyme specifically recognizes the Ile, Leu, Val, Phe, Met and Ala residues. Highly stable at room temperature, this enzyme has a molar mass of 34 kDa for 316 amino acids.

1.2—Activity: The Michaelis constant (of dissociation) of thermolysin is known for various protein and peptide substrates in the literature (MATSUBARA et al., *Biochem. Biophys. Res. Commun.*, vol. 21, p: 242-247, 1965). Based on these data, it is possible to deduce an average value of $K_p$ equal to 1 mM. The literature also describes the $k_{cat}$ values of thermolysin for various substrates (LIGNE et al., *Biochim. Biophys. Acta.*, vol. 1337, p: 143-148, 1997). Based on these data, it is also possible to determine an average value of $K_{cat}$ equal to 1000 min. The characteristics of thermolysin being known, an analysis of gelatine sequence makes it possible to determine that, in the studied system, the initial substrate concentration for thermolysin is therefore 0.15×0.45=0.68 mol.l$^{-1}$=68 mM or 68 $K_p$. This concentration is close to a saturated substrate concentration, the substrate does not therefore limit the reaction of the thermolysin.

The various enzymatic constraints of this enzyme were also measured using N-(3[2-furyl] acryloyl)-glycine-leucine-amide (SIGMA) as a substrate for the formation of Furyl-acroyl-glycine and Leucine-amide. The disappearance of the substrate during hydrolysis results in a reduction of the optical density measured at 345 nm.

2-Transqlutaminase:

2.1—Source: The transglutaminase used is produced by the company AJINOMOTO with the name ACTIVA WM®. This bacterial enzyme is produced in the *Streptoverticilium* sp culture medium. This enzyme is a polypeptide chain of 331 amino acids with a molecular weight de 38,000 Da. The cysteine residue in position 64 corresponds to the active site.

2.2—Activity: This enzyme recognises the lysine residues and catalyses the formation of covalent bonds between the side chains of the lysine residue and the side chains of other residue. The activity of this enzyme is optimum at a temperature of 50-55° C. (100 U.g$^{-1}$ at 40° C.), and in a broad pH range (activity from 4.5 to 9 with an optimum value between 6 and 7).

The activity of this enzyme is measured from the quantity of enzyme required to catalyse the formation of one micromole of hydroxamic acid for one minute at 40° C., from Na-CBZ-Gln-Gly (SIGMA) and hydroxylamine. The method that makes it possible to determine the activity of this enzyme is as follows:

| | |
|---|---|
| μl of enzyme in acetate buffer with pH 6 | 400 μl |
| NH2OH 2M | 25 μl |
| Nα-CBZ 0.1M | 75 μl |
| 10 min at 37° C. | |
| TCA 10% FeCl3 3% | 500 μl |
| Centrifugation 400 g 15 min | |
| DO 525 nm (blank with enzyme-free solution) | |

The activity is then calculated by the following equation:

$$\text{Activity}(U/ml/min) = [100 \times (DO525/238)]/\text{Enzyme vol. (ml)}$$

Various reactions on this substrate have made is possible to determine a dissociation constant $K_T$ of 8 mM and a $k_{cat}$ of 100 min$^{-1}$ using gelatine as a substrate. The gelatine only contains 4% of lysine; the initial substrate concentration for the transglutaminase is therefore 17 mM.

Modelling:

Based on the various values determined previously, it is possible to monitor the behaviour of the bonded fraction according to time by applying the Euler method of approximating differential equations (BRONSON, Equations Différentielles, Mc Graw-Hill ed, 1994). In this first model, the activity ratio between transglutaminase and protease is 10 (with a transglutaminase concentration of 1 U/ml). In addition, $g_0 = 0$ and $s_0 = 68$ mM. The data in the literature show that a gelatine gel is obtained by the action of transglutaminase when 18% of the theoretical bonds have effectively been created (FUCHSBAUER et al., *Biomaterials*, vol. 17, p: 1481-1488, 1999).

The various models show that the variation of V'$_p$ in relation to $V_p$ is of little importance and that the kinetics of the appearance of bonded proteins shows a considerable initial increase reaching values of almost 100%, followed by a very slow decrease which depends on the speed at which the small fragments appear. An example of modelling the evolution of the bonded fraction in time, with a V'$_p$/V$_p$ ratio of 0.1 is shown in FIG. 1.

1-3: Formation of a Gelatine Gel in the Presence of a Single Transglutaminase:

To validate this theoretical model, the inventors initially conducted a first series of experiments in which the formation of a gelatine gel was monitored in the presence of different quantities of transglutaminase only.

Polymerisable Proteins Used:

The type-A gelatine used (G2500) is extracted from pig skin using an acid method (SIGMA). The gelatine concentrations in the solution are expressed as a percentage (weight/volume). Thus, a solution with 1% gelatine corresponds to a solution of 1 g of gelatine in 100 ml of solution. The gelatine concentrations used varied in the experiments between 2 and 10% and the gelling temperature was 40° C.

The transglutaminase used is the previously described transglutaminase (see 1-2). The transglutaminase concentrations used in these experiments ranged from 0.1 U/ml to 1 U/ml.

Monitoring Solution/Gel and Gel/Solution Transitions:

The formation of a gel is monitored using an AR1000 (TA INSTRUMENT) or RS 150 (THERMORHEO) rheometer. These rheometers are mounted with 60-mm cone/plane geometries with an angle of 2°. A steel cone is used on the AR1000 and a titanium cone is used on the RS150.

These rheometers make it possible to perform an oscillating analysis or dynamic analysis, which consists of imposing on the sample an oscillating shear with a given pulse ω. During this movement, the shear stress and gradient evolve sinusoidally over time, with the same pulse, but with certain phase difference in relation to one another. The rheometers make it possible to measure numerous parameters for monitoring the gelling process. The shear modulus ($G^*_{(\omega)}0$) is a complex number which expresses the viscous and elastic component of the sample, and conforms to the following formula:

$$G^*_{(\omega)} = G'_{(\omega)} + iG''_{(\omega)}$$

G' is called storage modulus and G" is called loss modulus. These two moduli are expressed in Pascals (Pa). In a Newtonian liquid, the storage modulus is zero, only the loss modulus remains. This is why the loss modulus is sometimes also referred to as a viscous modulus. On the other hand, only the storage modulus exists in an elastic solid, which is why it is sometimes referred to as a solid modulus. It is possible to connect the shear modulus with the loss and storage moduli according to the following formulae:

$$G' = G^* \cos \delta \text{ and } G'' = G^* \sin \delta$$

Where δ represents the phase difference between the stress and the shearing deformation. Based on these formulae, the following ratio can be deduced:

$$\text{Tan } \delta = G''/G'$$

Tan δ then becomes a relevant value enabling characterisation of the sample gelling process. When the sample is liquid G">G' and Tan δ>1. Conversely, the sample becomes gel when G"<G' and Tan δ<1. The time taken to reach the value Tan S=1 represents the "gel time". In the various experiments below, the G"/G' moduli ratio for various solutions is expressed according to time, with the value G"/G'=1 corresponding to the "gel point".

Figure 2:
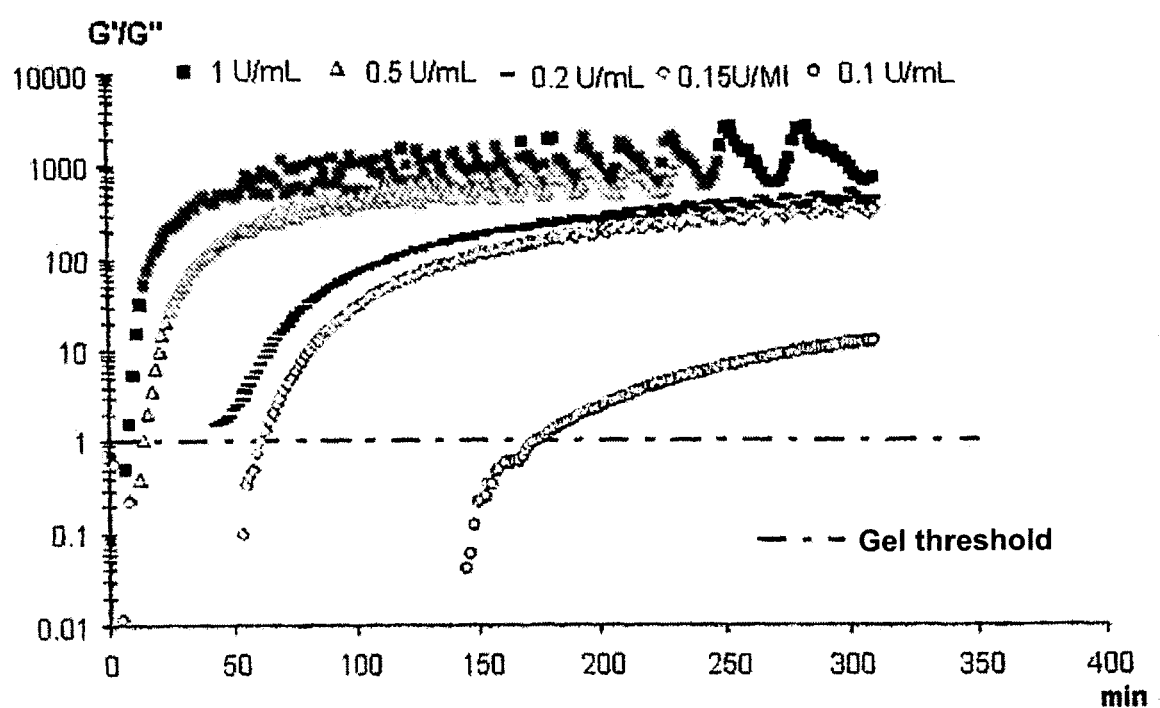
FIG. 2 relates to Example 1, section 1-3 "formation of a gelatine gel in the presence of a single transglutaminase", and shows the evolution of the viscoelastic properties, monitored using a rheometer, of a solution with 5% of gelatine at 40° C. and in the presence of various transglutaminase concentrations (0.1, 0.15, 0.2, 0.5 and 1 U/ml).

Results:

The evolution of the viscoelastic properties, monitored using a rheometer, of a solution with 5% of gelatine at 40° C. and in the presence of various transglutaminase concentrations (0.1, 0.15, 0.2, 0.5 and 1 U/ml) is presented in FIG. 2. It can be seen that, under all the tested conditions, the sample is actually liquid at the start of the experiment (G"/G'<1), a gel is then formed (G"/G'>1) and evolves over time. The experiments also show that after the gelling point and for any given enzyme concentration, the modulus G" levels off around 1 Pa. The values of the G' modulus therefore depend on the enzyme concentration. The variations in the G"/G' ratio observed after the gel point therefore show variations of G'.

Figure 3:
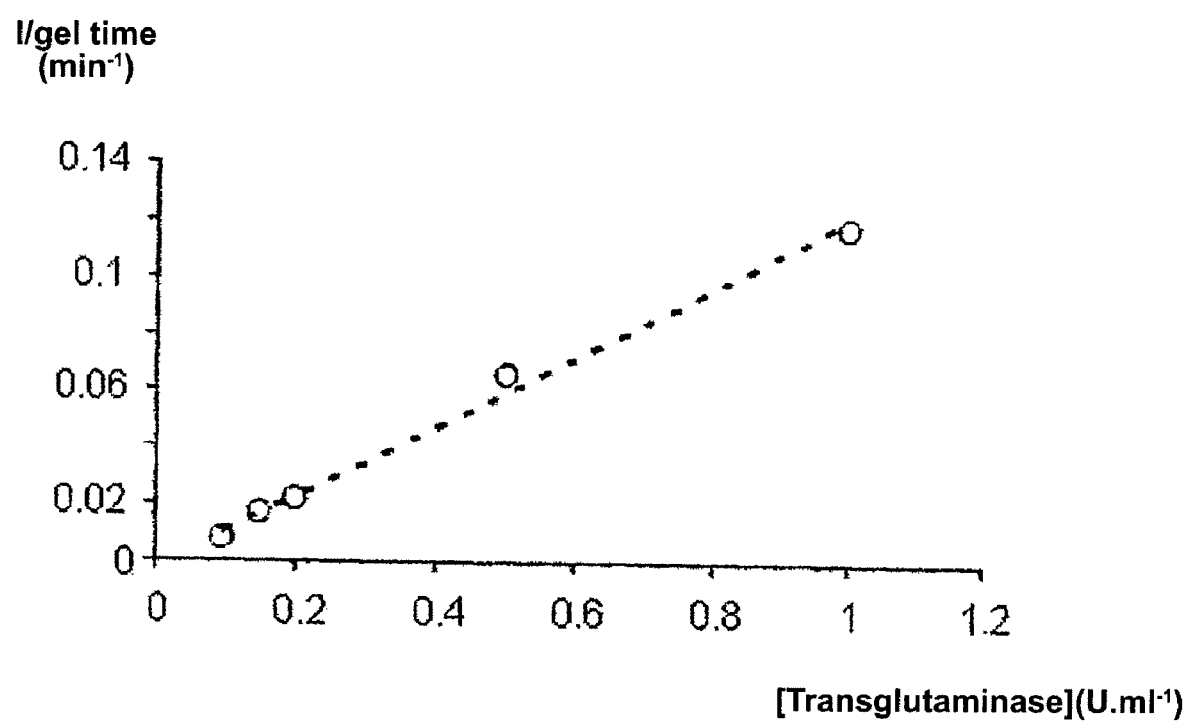
FIG. 3 relates to Example 1, section 1-3 "formation of a gelatine gel in the presence of a single transglutaminase", and shows the gelling speed (opposite of the gel time) of the solutions with 5% of gelatine at 40° C. according to the transglutaminase concentration.

FIG. 3 shows the gelling speed (opposite of the gel time) of the solutions with 5% of gelatine at 40° C. according to the transglutaminase concentration. The results show that the gelling curve conforms to the theoretical model, including only the step with the transglutaminase, and only up to the gel point where G"/G'=1.

Figure 4:
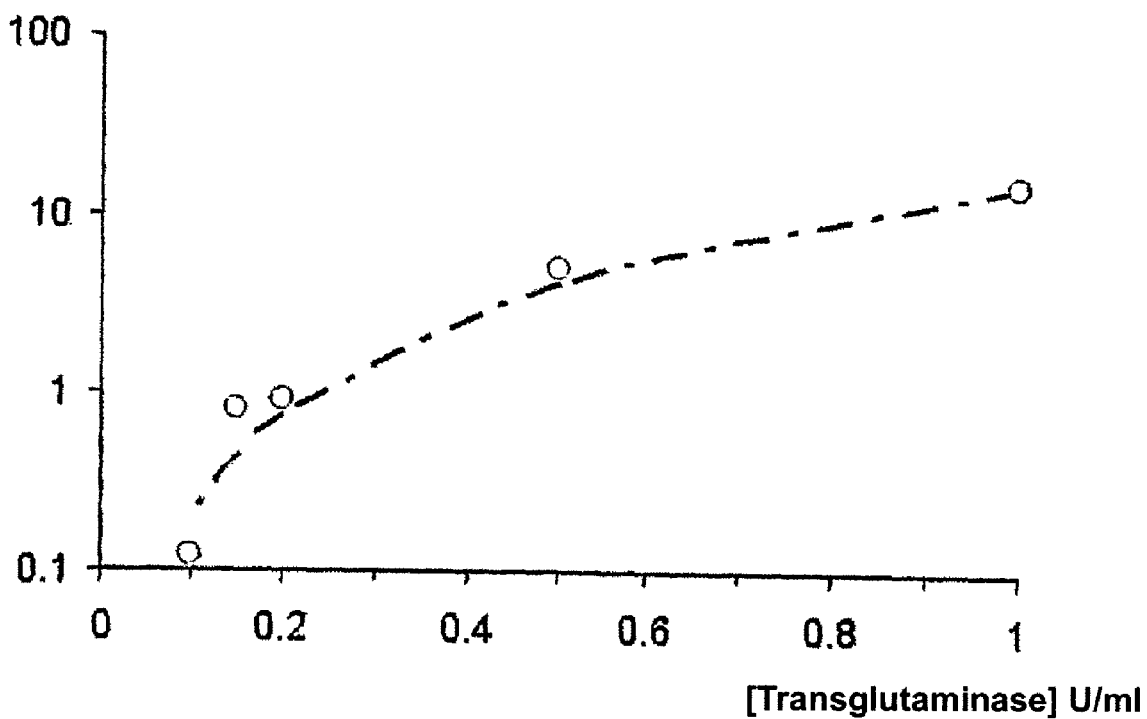
FIG. 4 relates to Example 1, section 1-3 "formation of a gelatine gel in the presence of a single transglutaminase", and shows the speed of enzymatic reaction depending on the enzyme concentration at 40° C., after the gel point.

FIG. 4 shows the speed of enzymatic reaction depending on the enzyme concentration at 40° C., after the gel point. The results show that, beyond the gel point, the gelling curve no longer conforms to the theoretical model. It can be seen that the curves can no longer be extrapolated by linear regression, but rather follow a behaviour pattern according to the power law with an equation $y = 15x^{1.85}$ (dotted curve in the figure) with an $R^2$ of 0.98. After the gel point, the enzymatic reaction is limited by the diffusion of the enzyme in the gel. The impact of diffusion is materialised in this speed equation by a coefficient of 1.85, which affects the transglutaminase concentration.

Figure 5:
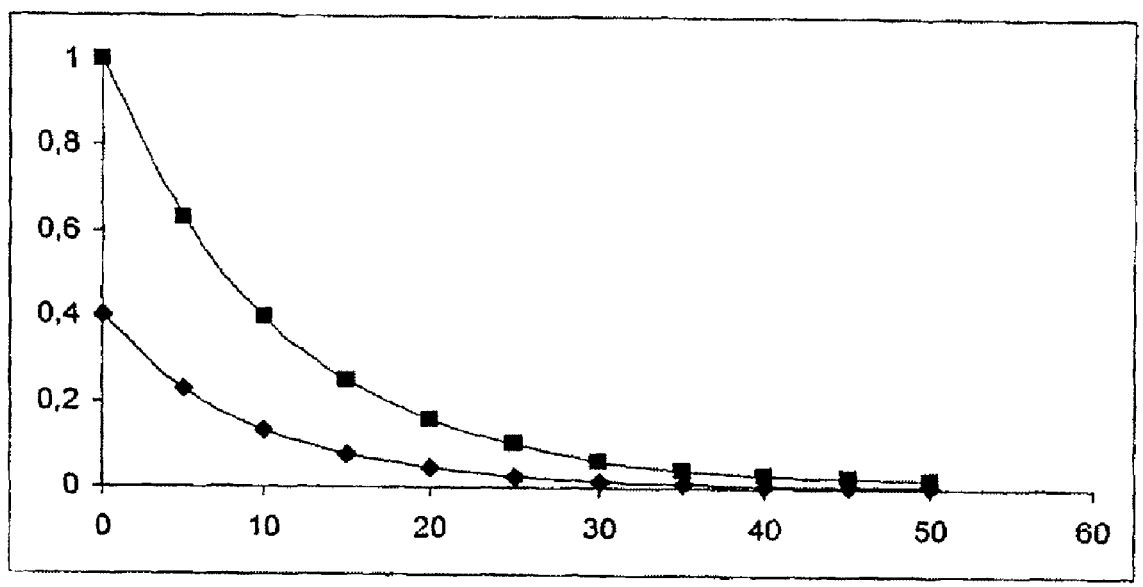
FIG. 5 relates to Example 1, section 1-3 "formation of a gelatine gel in the presence of a single transglutaminase", and shows the evolution, over time, of the quantity of active transglutaminase in the gel considering the diffusion for 1 unit (■) and 0.4 units (♦) of enzyme in solution.

FIG. 5 shows the evolution, over time, of the quantity of active transglutaminase in the gel considering the diffusion for 1 unit (■) and 0.4 units (◆) of enzyme in solution. These experiments have therefore made it possible to show that, after the formation of the gel, the value of the diffusion coefficient for the transglutaminase evolves gradually to reach the value of 1.85. This evolution of the diffusion coefficient can be easily determined from this curve and according to time.

It therefore seems that enzymatic action during gelling follows two successive systems. The first one, from liquid state to almost the gel point, is not limited by the diffusion and conventional enzymology rules apply. The speed of reaction is then a linear function of the enzyme concentration. The second one, after the gel point, is a non-conventional medium in which the speed of diffusion of the enzyme is no longer negligible and limits the apparent speed of reaction.

Experiments conducted on the gelatine gels with a presence of 2 and 10% of different transglutaminase concentrations have made it possible to confirm similar behaviour during gelling. In these conditions, each type of gel benefits from a specific diffusion coefficient which can be easily determined as above.

1-4: New Modelling of the Formation of a Gelatine Gel in the Presence of a Transglutaminase and Thermolysin:

A gelatine gel is modelled using the same parameters as described previously (see 1-2), with a $V_T/V_P$ ratio of 10 and a $V_P/V_p$ ratio of 0.05. However, the effect of restricting the diffusion of a gel with 5% of gelatine on the reaction speed of the enzyme is integrated in the previously described differential equations (see 1-2). Thus, the transglutaminase concentration is given an exponent of 1.85 in the equations that show the reaction balance as soon as the gel point is passed according to the following formula:

$$V_T = k_{CAT\_T}[T_0]^{1.85}$$

Previously conducted studies have shown that diffusion controlled the hydrolysis of gels only in the presence of very low enzyme concentrations, in particular less than 1 nM (FADDA et al., Biophys. J., vol. 85(5), p: 2808-2817, 2003), but not at greater concentrations (BERRY et al., Biochim. Biophys. Acta., vol. 1524, p: 110-117, 2000; GIRAUDIER et al., Biomacromolecules, vol. 5(5), p: 1662-1666, 2004). Therefore, no coefficient was applied to the thermolysin concentration in the equations.

Figure 6:
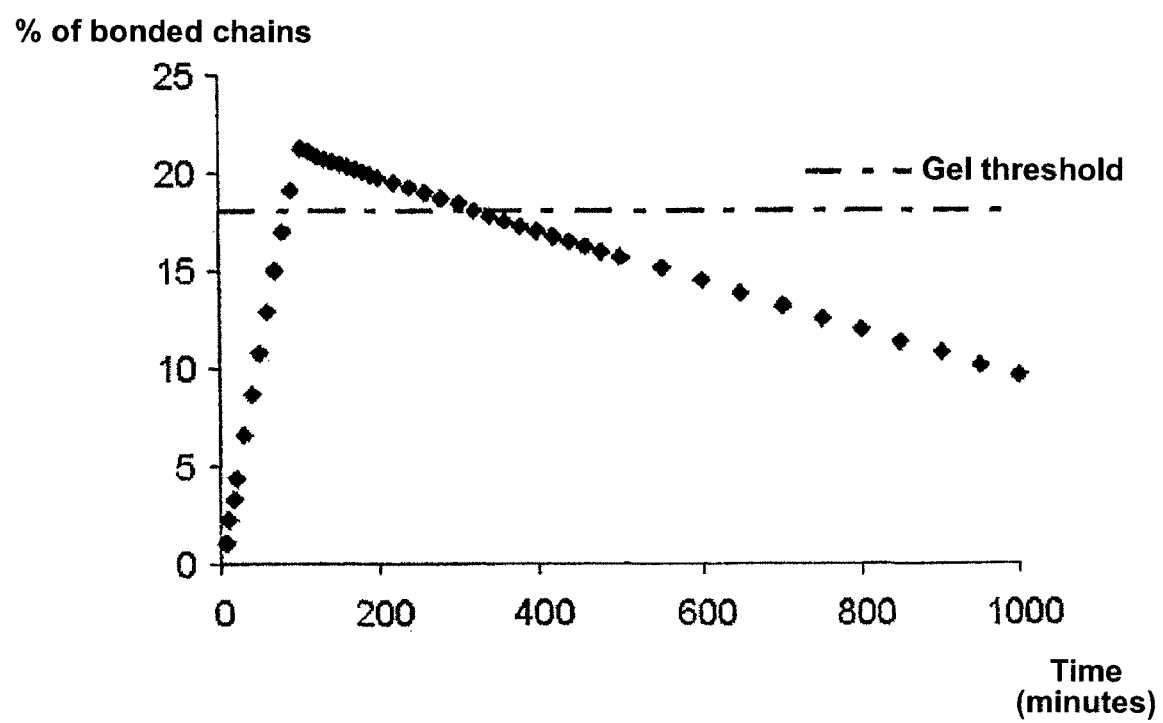
FIG. 6 relates to Example 1, section 1-4 "new modelling of the formation of a gelatine gel in the presence of a transglutaminase and thermolysin", and represents the result of modelling the evolution of the bonded fraction according to time with a diffusion restriction and a $V_T/V_P$ ratio of 10 (transglutaminase concentration of 1 U/ml).

FIG. 6 represents the result of modelling the evolution of the bonded fraction according to time with a diffusion restriction and a $V_T/V_P$ ratio of 10 (transglutaminase concentration of 1 U/ml). From this modelling process it emerges that the protein environment successively performs a solution/gel transition first passing the gel point after 80 minutes, followed by a gel/solution transition, passing the gel point for a second time after 330 minutes. According to the model established by the inventors, the protein environment that can be obtained has new properties, with the capacity successively to perform a solution/gel transition and then a gel/solution transition, with a gel state sustained for a period of 250 minutes.

Furthermore, the diffusion effect is considered to be all or nothing, in particular with no limitation prior to the gelling transition and with complete limitation after this transition. The previously conducted experiments (see 1-3) made it possible to show that the restrictions on diffusion increase as the network of covalent bonds develops in the gel. This gradual effect is taken into consideration in the model by using the following formula:

$V_T = k_{CAT\_T}[T_0]^\alpha$, where $\alpha$ varies according to time in a hyperbolic fashion from 1.1 to 1.85 (see FIG. 5).

Figure 7:
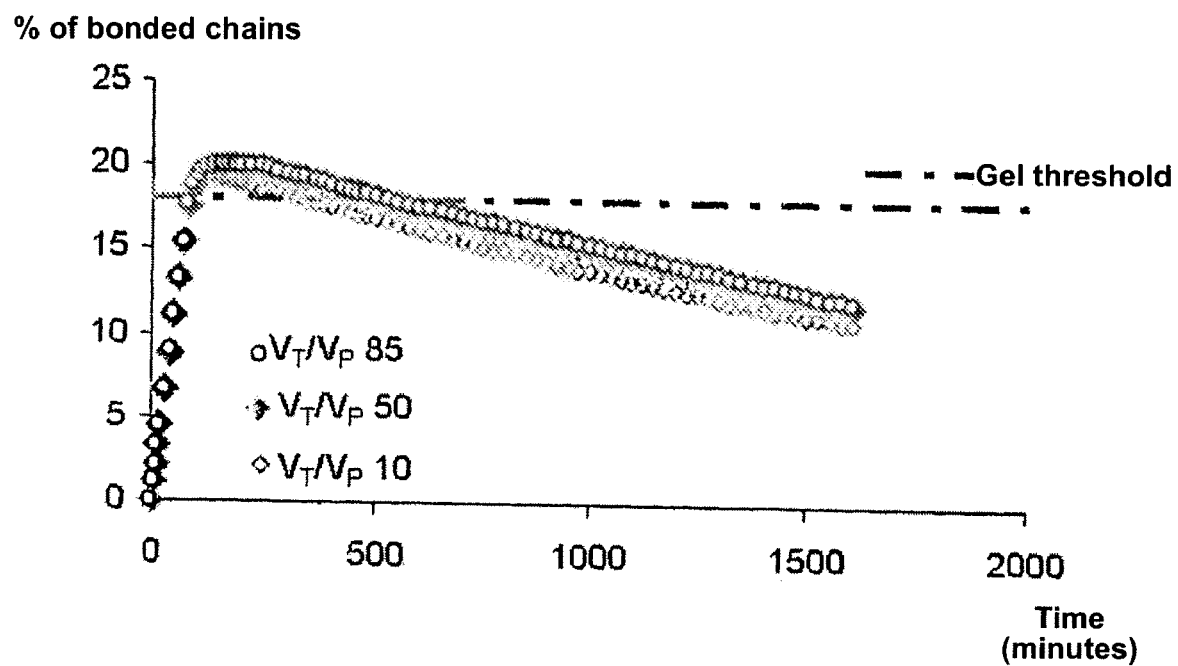
FIG. 7 relates to Example 1, section 1-4 "new modelling of the formation of a gelatine gel in the presence of a transglutaminase and thermolysin", and shows the result of modelling the evolution of the bonded fraction according to time with a gradual restriction of diffusion and various $V_T/V_P$ ratios (transglutaminase concentration of 1 U/ml).

FIG. 7 shows the result of modelling the evolution of the bonded fraction according to time with a gradual restriction of diffusion and various $V_T/V_P$ ratios (transglutaminase concentration of 1 U/ml). The results in this case also show solution/gel and gel/solution transitions for the various $V_T/V_P$ ratios shown. For the $V_T/V_P$ ratio of 10, the protein environment reaches the gel point in 15 minutes, the gel then performs a gel/solution transition after 165 minutes. With regard to the preceding model, a gradual restriction on diffusion makes it possible to obtain gel for 150 minutes, instead of 250 minutes as was previously the case.

1-5: Formation of a Gelatine Gel in the Simultaneous Presence of Transglutaminase and Thermolysin:

To validate the previously described theoretical model (see 1-4), various experiments were conducted using gelatine and transglutaminase in the same conditions as those used previously (see 1-3). In addition, a protease, thermolysin, is also added to the initial solution. The formation of gels was monitored according to time and at 40° C. according to the transglutaminase and thermolysin concentrations used. The results obtained, compared with the predictions of the theoretical model, are shown in table I below:

The various experiments also confirm the gel time and the useful gel life depending on the respective transglutaminase and thermolysin concentrations.

Figure 8:
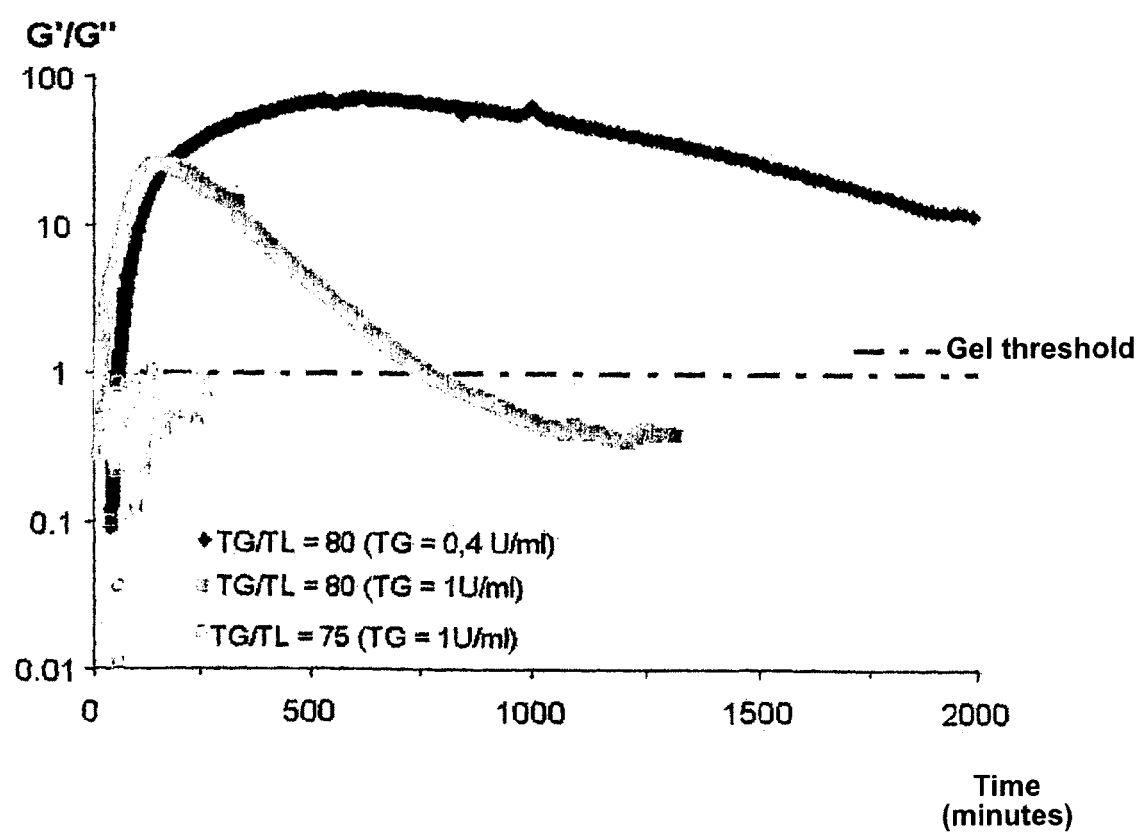
FIG. 8 relates to Example 1, section 1-5 "formation of a gelatine gel in the simultaneous presence of transglutaminase and thermolysin", and shows the experimental evolution of the viscoelastic properties of solutions with 5% of gelatine in the presence of different transglutaminase and thermolysin concentrations at 40° C.

FIG. 8 shows the experimental evolution of the viscoelastic properties of solutions with 5% of gelatine in the presence of different transglutaminase and thermolysin concentrations at 40° C.

In compliance with the theoretical model developed, it is therefore possible to obtain a biomaterial capable of successively performing a solution/gel transition and a gel/solution transition. For this, it is sufficient experimentally to determine the critical ratio of enzyme bonding the monomers to enzyme degrading the bonded monomers to obtain this first solution/gel transition according to the monomers and enzymes used. The theoretical model then makes it possible to adapt at least the various enzyme concentrations in order to obtain a gel that has, on the one hand, the desired gel time and, on the other hand, the desired useful gel life.

Additional experiments were conducted, in which 1% of alginate or oligoalginate was added to the solution with 5% of gelatine. In this case a solution/gel transition followed by a gel/solution transition was also obtained.

1-6: Formation of a Gelatine Gel in the Simultaneous Presence of Transglutaminase and Various Proteases:

Various proteases were used to confirm the developed model.

Trypsin, EC 3-4-21-4, is a serin protease which hydrolyses peptide bonds upstream from the lysines and arginines. The trypsin used comes from cow pancreas and is marketed by Sigma (T-1426). The activity of this enzyme is measured according to the quantity of enzyme required to catalyse the hydrolysis of p-tosyl arginine methyl ester (Sigma T4626).

Collagenase (EC 3.4.24.3) specifically hydrolyses the X-Gly peptide bonds in the Pro-X-Gly-Pro (SEQ ID NO: 1) sequences, which can be found in particular in chains containing collage. The collagenase used is obtained from type IA Clostridium histolyticum and marketed by Sigma

TABLE I

| | | | Theoretical | | | Experimental | | |
|---|---|---|---|---|---|---|---|---|
| TGase/ Thermolysin ratio | TGase (in U/ml) | Thermolysin (in U/ml) | Gel formation | Gel time (min) | Useful gel life (min) | Gel formation | Gel time (min) | Useful gel life (min) |
| 10 | 0.4 | 0.04 | yes | 35 | 270 | no | — | — |
| 10 | 1 | 0.1 | yes | 15 | 150 | no | — | — |
| 60 | 0.4 | 0.0067 | yes | 35 | 1,600 | no | — | — |
| 60 | 1 | 0.0167 | yes | 15 | 875 | no | — | — |
| 75 | 0.4 | 0.0053 | yes | 35 | 2,000 | no | — | — |
| 75 | 1 | 0.013 | yes | 15 | 1,150 | no | — | — |
| 80 | 0.4 | 0.005 | yes | 40 | 3,000 | yes | 56 | >4,800 |
| 80 | 1 | 0.0125 | yes | 15 | 1,200 | yes | 19 | 743 |

The results show that, in compliance with the theoretical model developed, it is possible experimentally to obtain, from a solution of monomers that can be polymerised by covalent bonds in the presence of two antagonising enzymatic activities (in this case a solution with 5% of gelatine in the presence of different transglutaminase and thermolysin concentrations) a solution/gel transition then a gel/solution transition successively.

If such a gel is obtained in all the simulations after a time that only depends on the transglutaminase activity, the various experiments show that there is a $V_T/V_P$ ratio that constitutes a threshold value for the first solution/gel transition. In the case of a solution with 5% of gelatine in the presence of transglutaminase and thermolysin, the critical $V_T/V_P$ ratio to obtain this first solution/gel transition is comprised between 75 and 80.

(C-9891). The activity of this enzyme is measured according to the quantity of enzyme required to catalyse the hydrolysis of N-(3-[2-furyl]acryloyl)-Leu-Gly-Pro-Ala (SEQ ID NO: 2) or FALGPA (Sigma F-5135).

Since these enzymatic activities are measured on the hydrolysis of synthetic peptides having a chromophore group, the activity of the thermolysin was measured on the hydrolysis of N-(3-(2-furyllacryloyl)-Gly-Leu-amide (Sigma N-7383) for improved comparison. This is the activity reported in the tables with several proteases.

For gels, the gelatine concentration was 7% and the gelling temperature was 40° C. The transglutaminase used is the previously described transglutaminase. The gels were monitored over time as in 1-5. The results obtained are shown in table II below:

TABLE II

| TGase/Protease ratio | TGase (in U/ml) | Protease (in U/ml) | Gel formation | Gel time (min) | Useful gel life (min) |
|---|---|---|---|---|---|
| 375 | 1.5 | 0.004 (16 nM thermolysin) | yes | 24 | 546 |
| 48 | 1.5 | 0.031 (31 nM trypsin) | yes | 14 | 396 |
| 520 | 1.5 | 0.003 (16 nM collagenase) | yes | 8 | 492 |

The results therefore show that the model can be generalised for other proteases.

Example 2

Physical Gel 2-1: Development of a Theoretical Model:

This model shows the dynamic balance observed only in the case of forming a physical gel and in the presence of a single enzymatic activity. Gelling therefore results only from the formation of low-energy bonds (Van der Waals, hydrogen bonds, hydrophobic bonds, etc.; H) between monomers in solution (s). In the case of proteins, for example, their polyelectrolyte properties means they are almost all capable of forming physical gels. The degradation of polymers corresponding to chains of bonded monomers (g) of the gel is catalysed by an enzyme (P) which hydrolyses them in soluble monomers (s). Finally, in certain cases, there exists a third reaction also catalysed by the enzyme (P) which consists of hydrolysing soluble monomers into degraded monomers (f) which are too small to be a part of the network or which can no longer form bonds with other soluble monomers. This last reaction which results in monomers leaking from the cycle is also added to the model. The model can be easily represented according to the following reaction scheme:

Scheme II:
Enzyme degrading the chains of bonded monomers (P)

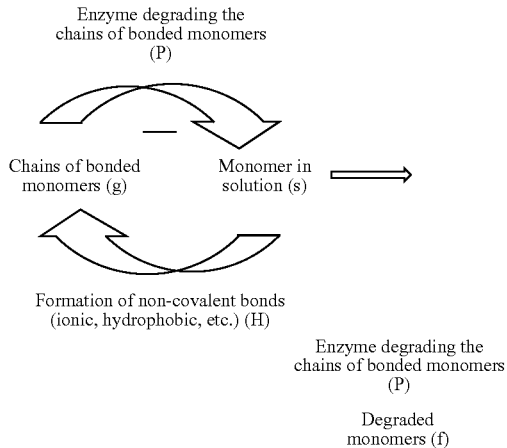

In this second case, the reaction mechanism can be easily described by the following three differential equations, where the enzymatic reactions are compared with simple Michaelian reactions and by a fourth mass conservation equation.

The differential equation that describes the evolution of the number of chains of bonded monomers (g) according to time is as follows:

$$\frac{dg}{dt} = -\frac{V_P}{K_P + g} \times g + V_H$$

The differential equation that describes the evolution of the number of monomers in solution (s) according to time is as follows:

$$\frac{ds}{dt} = \frac{V_P}{K_P + g} \times g - \frac{V'_P}{K_P + s} \times s - V_H$$

The differential equation that describes the evolution of the number of degraded monomers (f) according to time is as follows:

$$\frac{df}{dt} = \frac{V'_P}{K_P + s} \times s$$

Finally, the mass conservation equation remains unchanged:

$$g_t + s_t + f_t = S_0$$

In these differential equations, $V_P$ represents the maximum speed for the enzyme degrading the monomers and $K_P$ represents the Michealis constant for this same enzyme.

In these differential equations, $V_P$ is calculated according to the following equation:

$$V_P = k_{cat\_P}[P_0]$$

Moreover, $V_H$, which represents the speed of formation of the low-energy bonds, depends on the monomer used.

In the transposition of this equation to an in vitro system, the various values of [P], [T], $V_p$, $V_H$ and $K_P$ are constants.

The substrate concentrations are calculated at the start and are then determined during the reaction by means of the various differential equations.

2-2: Modelling the Formation of a Physical Gelatine Gel at 27° C. in the Presence of Thermolysin:

This theoretical model was applied to the formation of a physical protein gel, more specifically of gelatine at 27° C., in the presence of thermolysin. At this temperature, the gelatine forms a gel by partial association of the monomers in triple helices. These triple helices, stabilised by hydrogen bonds, appear by lowering the temperature.

Gelatine:

1-Description: Gelatine is obtained from collagen. Collagen is synthesised in the form of large precursors: a prochains. The formation of pro-collagen entails the assembly of three α pro-chains by hydrogen bonds and the hydroxylation of certain proline and lysine residues to form hydroxyproline and hydroxylysine respectively. Finally, after secreting the pro-collagen in the extracellular environment, the pro-collagen is aged by cleaving the pro-peptides to form collagen. The latter is then capable of associating with other collagen molecules to form collagen fibrils, which aggregate to form collagen fibres. The stability of the triple helix formed by the association of the three α pro-chains depends on the organism from which it is taken. The denaturation temperature (Tm) therefore ranges from 41.5° C. for certain mammals to 6° C. for certain fish living in Arctic waters. The Tm variation is correlated to the level of hydroxyproline in the molecule (PERSIKOV et al., *Biochemistry*, vol. 39, p: 14960-14967, 2000).

Gelatine is obtained by an acid or alkaline treatment of tissue containing collagen, which results in denaturation of the collagen triple helix (PEZRON, *physical Networks*., Londres Elsevier Applied Science, 1990). In this study, the gelatine used is type-A gelatine obtained by an acid treatment.

When the semi-diluted gelatine solution is chilled below the denaturation temperature of the collagen chains, a gel is formed. The chains then associate to form triple-helical portions similar to those of the native collagen. This conformational transition enables the creation of a three-dimensional network that traps the water molecules present. The gel formed is therefore a physical gel in which the triple helices are only stabilised by hydrogen bonds (weak bonds). These bonds can be destabilised by increasing the temperature, which causes the dissolution of the gel: this gelling phenomenon is therefore reversible.

Previous studies have shown that the elasticity of this gel depends only on the concentration of helices in the sample (JOLY-DUHAMEL et al., *Langmuir*, vol. 18, p: 7158-7166, 2002; JOLY-DUHAMEL et al., *Langmuir*, vol. 18, p: 7208-7217, 2002).

2-Concentration: The gelatine concentration used is the same as that described in example 1.

3-Speed of helix formation: The speed of formation of the triple helices ($V_H$) was determined by monitoring the change of the ball/helix conformation by polarimetry according to time or temperature. Indeed, the slight twist resulting from the formation of the triple helix causes a slight rotation of polarised light passing through the sample. This study was performed using a PERKIN ELMER 341 polarimeter or a JASCO 1100 polarimeter. The measurements were taken at 436 nm.

Figure 9:
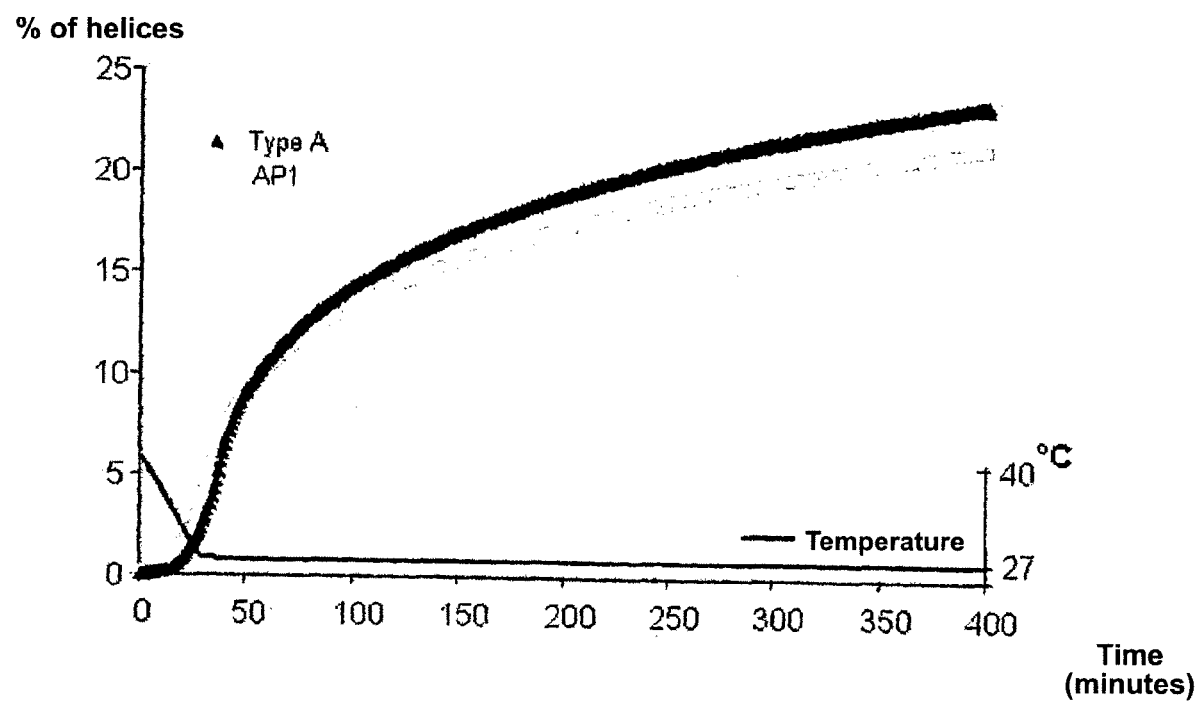
FIG. 9 relates to Example 2, section 3 "Speed of helix formation", and shows the evolution of the percentage of helices of solutions with 5% of the two type-A gelatines used (type A and AP1) according to time and with cooling from 40° C. to 27° C. at a rate of 0.5° C./minute.

The study by polarimetry of the formation kinetics of a type-A gelatine (type A or AP1) makes it possible to determine, for each gelatine, the evolution of the percentage of helices according to time at 27° C. FIG. 9 shows the evolution of the percentage of helices of solutions with 5% of the two type-A gelatines used (type A and AP1) according to time and with cooling from 40° C. to 27° C. at a rate of 0.5° C./minute.

The results of the appearance kinetics are generally identical in both samples. At the gel time, the percentage of helices is identical for the two gelatines (6.4% at 40 minutes).

Figure 10:
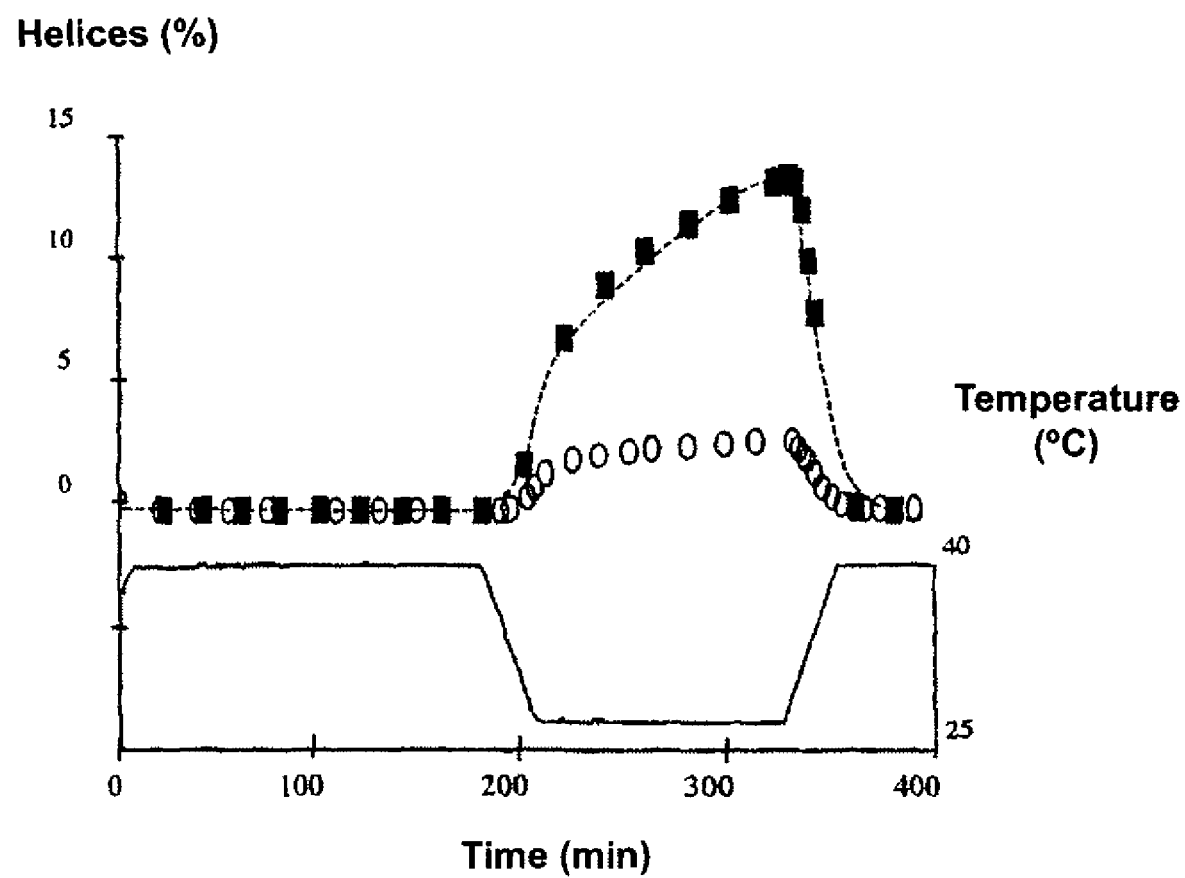
FIG. 10 relates to Example 2, section 3 "Speed of helix formation", and also shows the evolution of the percentage of helices according to time and temperature for a physical gel with no transglutaminase (full boxes) and for a chemical gel obtained in the presence of transglutaminase (empty circles).

The speed of formation of the helices can be calculated easily from FIG. 9. FIG. 10 also shows the evolution of the percentage of helices according to time and temperature for a physical gel with no transglutaminase (full boxes) and for a chemical gel obtained in the presence of transglutaminase (empty circles). The speed of appearance of the helices was determined over various time intervals and used in the model. Thus, for FIG. 10 and for the physical gel, $V_H$ is 45 $10^{-5}$ M.min$^{-1}$ during 10 minutes, 21 $10^{-5}$ M.min$^{-1}$ during 10 minutes, 9 $10^{-5}$ M.min$^{-1}$ during 20 minutes, and then 4.5 $10^{-5}$ M.min$^{-1}$ during the next 90 minutes and finally 2.5 $10^{-5}$ M.min$^{-1}$.

Similar experiments were conducted using gels containing 2 to 10% of gelatine.

Enzymes:

The protease used is the thermolysin used in example 1. The same parameters as above are therefore used. However, the different sensitivity of the two enzymes at this temperature is taken into consideration:

For TL ($V_{i40°\ c.} = 1.66 V_{i27°\ c.}$)

For TG ($V_{i40°\ c.} = 2.68 V_{i27°\ c.}$)

Modelling:

Based on the various values determined previously, it is possible to monitor the behaviour of the bonded fraction according to time by applying the Euler approximation method for resolving differential equations as above. Several modelling experiments were conducted using different thermolysin concentrations.

Figure 11:
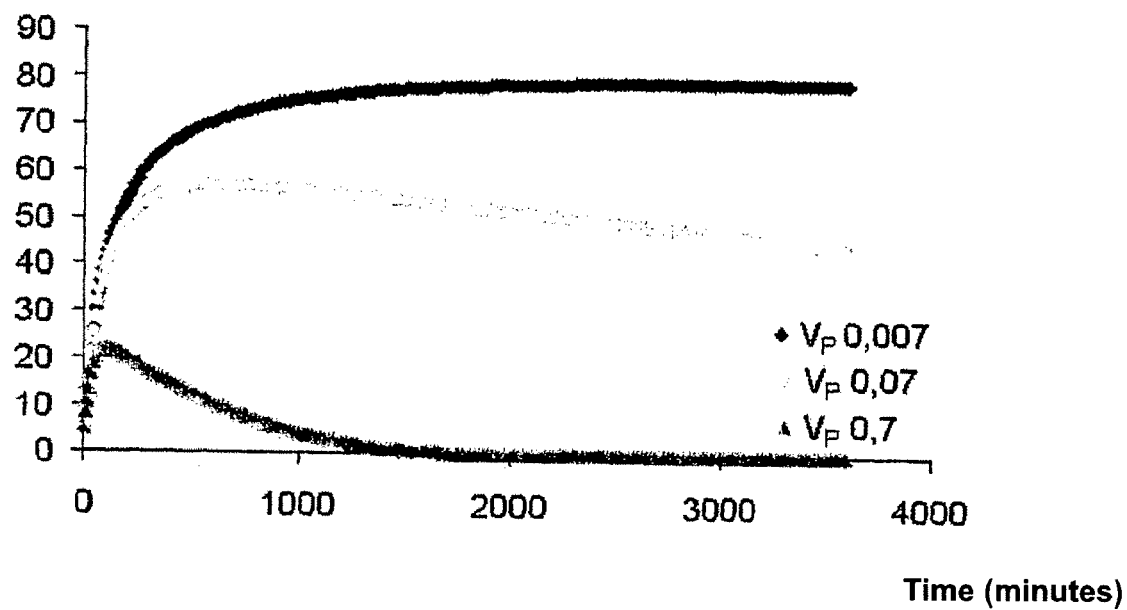
FIG. 11 relates to Example 2, and presents several examples of modelling the evolution of the percentage of bonded chains in the presence of different thermolysin concentrations at 27° C. (the gel threshold is 6.4% of helices).

FIG. 11 presents several examples of modelling the evolution of the percentage of bonded chains in the presence of different thermolysin concentrations at 27° C. (the gel threshold is 6.4% of helices). The results obtained show that a transition is possible for certain values of $V_P$ and that, in every case, the leak of small fragments due to hydrolysis results in degradation of the network and, therefore, to solubilisation of the formed gel.

2-3: Formation of a Physical Gelatine Gel in the Presence of Thermolysin:

To validate this theoretical model, various experiments were conducted according to the same method as described above (see 2-2), adding different thermolysin concentrations. The results obtained, compared with the predictions of the theoretical model, are shown in table III below:

TABLE III

| Thermolysin (in U/ml) | Theoretical | | | Experimental | | |
|---|---|---|---|---|---|---|
| | Gel formation | Gel time (min) | Useful gel life (units) | Gel formation | Gel time (min) | Useful gel life (min) |
| 0.1 | no | | | | | |
| 0.02 | no | | | | | |
| 0.015 | no | | | | | |
| 0.0125 | yes | 110 | 5,000 | | | |
| 0.01 | yes | 110 | 6,000 | no | — | — |
| 0.004 | | 110 | 20,000 | yes | 45 | approx. 4,300 |
| 0.0085 | | 110 | 9,000 | yes | 68 | 254 |

The results in this case also show that, in compliance with the theoretical model developed, it is possible experimentally to obtain a solution/gel transition followed by a successive gel/solution transition, and to do so from a solution of monomers that can polymerise by the formation of low-energy bonds and in the presence of an enzyme capable of degrading the bonded polymer chains (in this case, a solution with 5% of gelatine at 27° C. in the presence of various thermolysin concentrations).

It is observed that with every thermolysin concentration tested (from 0.001 to 0.1 U/ml), the gel, when formed, ends up melting, which agrees with the theoretical model developed.

In the case of a solution with 5% of gelatine at 27° C. and in the presence of thermolysin, the critical thermolysin concentration for obtaining a first solution/gel transition is 0.01 units.

The gel time then also depends on the thermolysin concentration used.

Figure 12:
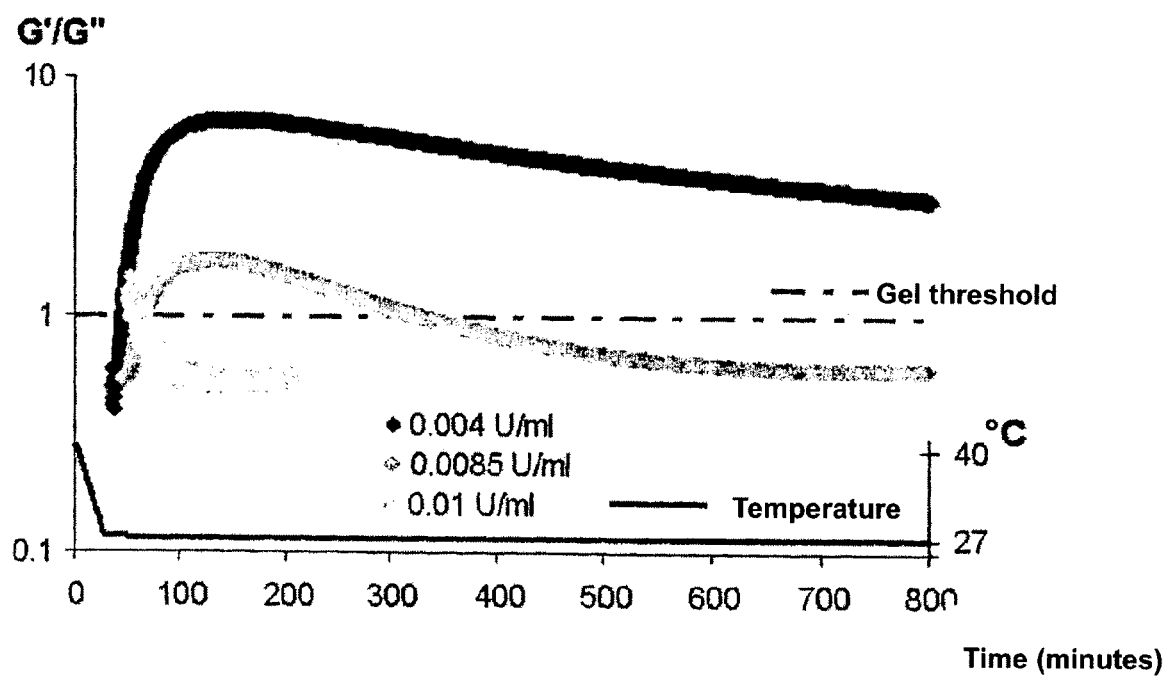
FIG. 12 relates to Example 2, section 2-3 "formation of a physical gelatine gel in the presence of thermolysin", and shows the experimental evolution of the viscoelastic properties of solutions with 5% of gelatine in the presence of different thermolysin concentrations at 27° C.

FIG. 12 shows the experimental evolution of the viscoelastic properties of solutions with 5% of gelatine in the presence of different thermolysin concentrations at 27° C.

In compliance with the theoretical model developed, it is therefore possible to obtain a biomaterial capable of successively performing a solution/gel transition and a gel/solution transition. For this purpose, it is sufficient to determine the critical concentration of enzyme capable of degrading the chains of monomers bonded by low-energy interactions. The theoretical model then makes it possible to adapt the enzyme concentration to obtain a gel that has, on the one hand, the desired gel time and, on the other hand, the desired useful gel life.

Example 3

Mixed Gel

3-1. Development of a Theoretical Model:

This integral model corresponds to the dynamic balance obtained by the formation of a mixed gel (physical and chemical) in the presence of two antagonising enzymatic activities. The model can be simply represented according to the following reaction scheme (integrating data from schemes I and II):

Scheme III:

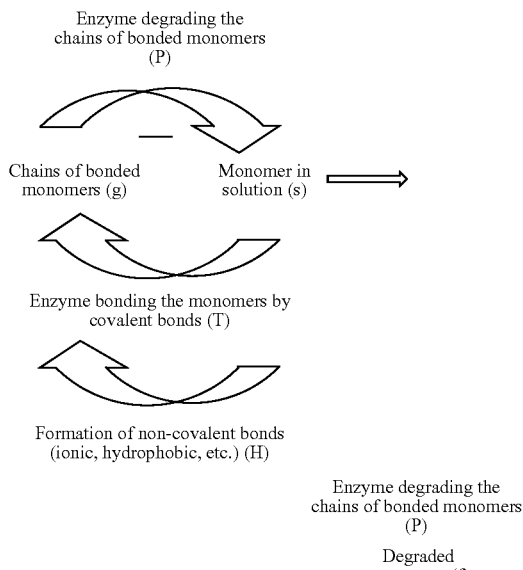

In this third case, the reaction mechanism can be easily described by the following three differential equations, where the enzymatic reactions are compared with simple Michaelian reactions and by a fourth mass conservation equation.

The differential equation that describes the evolution of the number of chains of bonded monomers (g) according to time is as follows:

$$\frac{dg}{dt} = -\frac{V_P}{K_P+g} \times g + \frac{V_T}{K_T+s} \times s + V_H$$

The differential equation that describes the evolution of the number of monomers in solution (s) according to time is as follows:

$$\frac{ds}{dt} = \frac{V_P}{K_P+g} \times g - \frac{V_T}{K_T+s} \times s - \frac{V'_P}{K_P+s} \times s - V_H$$

The differential equation that describes the evolution of the number of degraded monomers (f) according to time is as follows:

$$\frac{df}{dt} = \frac{V'_P}{K_P+s} \times s$$

Finally, the mass conservation equation is as follows:

$$g_t + s_t + f_t = S_0$$

In these differential equations, $V_H$ represents the speed of formation of the low-energy bonds and depends on the monomer used, $V_P$ and $V_T$ represent the maximum speeds for enzymes P and T respectively, and $K_P$ and $K_T$ represent the Michaelis constants for enzymes P and T respectively.

In the transposition of this equation to an in vitro system, the various values of [P], [T], $V_P$, $V_T$, $K_P$ and $K_T$ are constants.

3-2: Modelling the Formation of a Mixed Gelatine Gel at 27° C. in the Presence of Transglutaminase and Thermolysin:

This theoretical model was applied to the formation of a mixed protein gel, more specifically of gelatine at 27° C., and in the presence of transglutaminase and thermolysin.

Gelatine:

The same gelatine concentration as in examples 1 and 2 is used. The speed of helix formation is the same as described in example 2.

Enzymes:

The protease used is the thermolysin used in examples 1 and 2.

The transglutaminase is the same as that used in example 1. The diffusion coefficients were integrated as described in example 1 to take into account the effect of diffusion on the activity of the transglutaminase.

The parameters used for these two enzymes are therefore the same as described previously.

Modelling:

Based on the various values determined previously, it is possible to monitor the behaviour of the bonded fraction according to time by applying the Euler method for approximation of the differential equations as above. Several modelling experiments were conducted using different transglutaminase and thermolysin concentrations. A diffusion coefficient was applied for transglutaminase as described in example 1.

Figure 13:
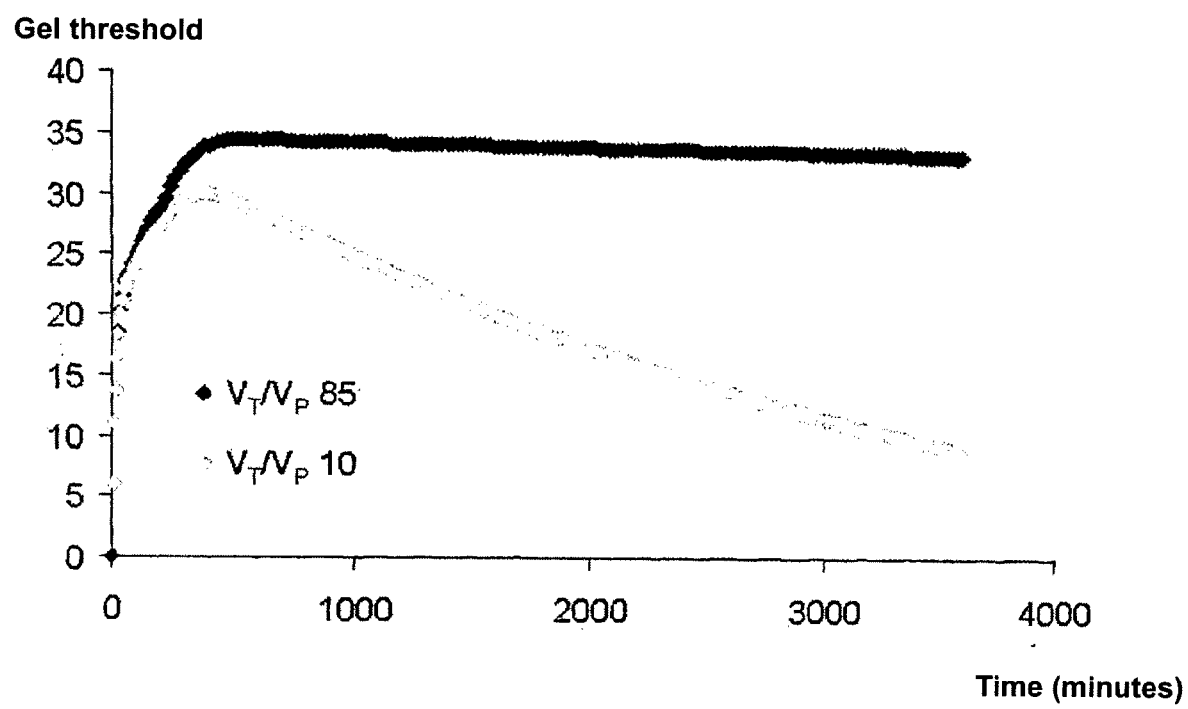
FIG. 13 relates to Example 3, section 3-2 "modelling the formation of a mixed gelatine gel at 27° C. in the presence of transglutaminase and thermolysin", and shows the evolution of the fraction of bonded monomers according to time and for different $V_T/V_P$ ratios (with a transglutaminase concentration of 1 U/ml).

FIG. 13 shows the evolution of the fraction of bonded monomers according to time and for different $V_T/V_P$ ratios (with a transglutaminase concentration of 1 U/ml).

The results suggest, on the one hand, that gelling occurs faster than in the preceding examples and, on the other hand, that the fraction of bonded monomers and the stability of the gels are more important here than in physical or chemical gels.

3-3: Formation of a Mixed Gelatine Gel in the Presence of Thermolysin:

To validate the previously described theoretical model, an experiment was conducted on a sample with 5% of gelatine at 40° C., in the presence of two transglutaminase and thermolysin enzymes with a transglutaminase/thermolysin ratio of 80 and a transglutaminase concentration of 1 U/ml. The solution was cooled from 40° C. to 27° C. at a rate of 0.5° C. per minute. The evolution of the gelatine solution was simultaneously monitored by rheology and by polarimetry as described above. The results obtained, compared with the predictions of the theoretical model, are shown in table IV below:

TABLE IV

| TGase to Thermo-lysin ratio | TGase (in U/ml) | Thermo-lysin (in U/ml) | Theoretical | | | Experimental | | |
|---|---|---|---|---|---|---|---|---|
| | | | Gel forma-tion | Gel time (min) | Useful Gel life (min) | Gel forma-tion | Gel time (min) | Useful gel life (min) |
| 80 | 1 | 0.0125 | yes | <5 | 15,000 | yes | 2 | >5,000 |
| 80 | 0.4 | 0.005 | yes | 15 | >17,000 | nd | | |
| 50 | 1 | 0.02 | yes | <5 | 5,000 | nd | | |
| 50 | 0.4 | 0.008 | yes | 15 | 9,000 | nd | | |
| 10 | 1 | 0.1 | yes | <5 | 750 | nd | | |
| 10 | 0.4 | 0.04 | yes | 15 | 1,000 | nd | | | nd: not determined

The results show that, in compliance with the theoretical model developed, it is possible experimentally to obtain, from a solution of monomers that can be polymerised by low-energy bonds and by covalent bonds, and in the presence of two antagonising enzymatic activities (in this case, a solution with 5% of gelatine at 27° C. and in the presence of different transglutaminase and thermolysin concentrations), a solution/gel transition then a gel/solution transition successively.

In compliance with the theoretical model developed, the gel formation time is very quick. In addition, the stability and the useful life of the "mixed" gel obtained are very high compared with both the physical and chemical gels.

Figure 14:
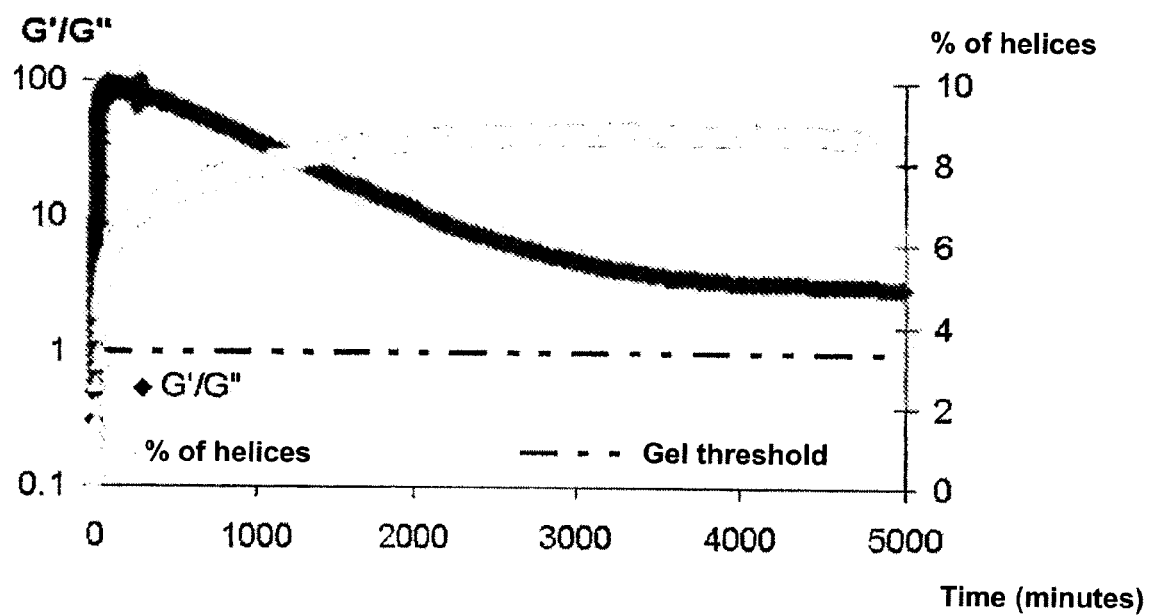
FIG. 14 relates to Example 3, section 3-3 "formation of a mixed gelatine gel in the presence of thermolysin", and shows the simultaneous evolution of the viscoelastic properties and the helical percentage of a solution with 5% of gelatine in the presence of transglutaminase and thermolysin, with a transglutaminase/thermolysin ratio of 80 and a transglutaminase concentration of 1 U/ml, and at 27° C.

FIG. 14 shows the simultaneous evolution of the viscoelastic properties and the helical percentage of a solution with 5% of gelatine in the presence of transglutaminase and thermolysin, with a transglutaminase/thermolysin ratio of 80 and a transglutaminase concentration of 1 U/ml, and at 27° C.

In compliance with the theoretical model developed, which is based on the two previous theoretical models, it is possible to obtain a biomaterial capable of successively performing a solution/gel transition and a gel/solution transition. For this, it is sufficient experimentally to determine the critical ratio of enzyme bonding the monomers/enzyme degrading the bonded monomers as in example 1 in order to obtain a first solution/gel transition according to the monomers and enzymes used. The theoretical model then makes it possible to adapt the various enzyme concentrations in order to obtain a gel that has, on the one hand, the desired gel time and, on the other hand, the desired useful gel life.

3-4: Formation of a Physical Gelatine Gel in the Presence of Various Proteases:

To confirm the results obtained in 3-3, experiments were conducted on samples with 7% of gelatine at 40° C., in the presence of transglutaminase and various proteases with a transglutaminase concentration of 1.5 U/ml. The solution was cooled from 40° C. to 27° C. at a rate of 0.5° C. per minute. The evolution of the gelatine solution was simultaneously monitored by rheology and by polarimetry as described above. The results obtained are shown in table V below:

TABLE IV

| Ratio of TGase to Protease | TGase (in U/ml) | Protease (in U/ml) | Experimental | | |
|---|---|---|---|---|---|
| | | | Gel formation | Gel time (min) | Useful gel life (min) |
| 115 | 1.5 | 0.013 Thermolysin | yes | 46 | 404 |
| 14 | 1.5 | 0.11 Trypsin | yes | 48 | >1,500 |
| 3,750 | 1.5 | 0.0004 collagenase) | yes | 26 | 475 |

These results also show that the model developed can be generalised for other enzymes.

The invention claimed is:

1. A method for preparing a biomaterial comprising mixing in a suitable solvent:
   (i) a plurality of monomers that form polymers, or a mixture of monomers and their polymers; and
   (ii) an enzyme that degrades the polymers;
   wherein the biomaterial is present either in the form of a gel or in the form of a solution, and performs a first solution/gel transition by polymerization and then, under the action of the enzyme, performs a second gel/solution transition and
   wherein the quantity of monomers that forms polymers is between 0.1 and 30% by weight of the total weight of the biomaterial.

2. The method of claim 1 further comprising mixing in a suitable solvent:
   a second type of enzyme that forms covalent bonds between the monomers.

3. The method of claim 1 or 2, wherein the suitable solvent is an aqueous solvent.

4. The method of claim 2, wherein the ratio of the concentration of enzymes that form covalent bonds between the monomers to the concentration of enzymes that degrade the polymers is greater than or equal to 1.

5. The method of claim 2, wherein the concentration of enzymes that form covalent bonds between the monomers is greater than 0.001 U/ml.

6. The method of claim 1 or 2, further comprising lyophilising the biomaterial in gel form.

7. The method of claim 2, wherein the concentration of monomers that form polymers, the concentration of enzyme that degrades the polymers and, optionally, the concentration of enzyme that forms covalent bonds between the monomers are chosen so as to obtain a biomaterial with a desired gel time and a useful gel life.

8. The method of claim 1, wherein the monomers polymerize by reducing the temperature of the mixture.

9. The method of claim 1, wherein the monomers are identical.

10. The method of claim 1, wherein the monomers are different.

* * * * *